United States Patent
Pham et al.

(10) Patent No.: US 11,938,178 B2
(45) Date of Patent: Mar. 26, 2024

(54) OPTIMIZED EPICUTANEOUS VACCINATION

(71) Applicants: DBV TECHNOLOGIES, Montrouge (FR); BIONET-ASIA CO., LTD, Bangkok (TH)

(72) Inventors: Hong Thai Pham, Bangkok (TH); Nathalie Donne, Allauch (FR); Pierre-Louis Herve, Montrouge (FR); Lucie Mondoulet, Chatillon (FR)

(73) Assignees: DBV TECHNOLOGIES, Montrouge (FR); BIONET-ASIA CO., LTD, Bangkok (TH)

( * ) Notice: Subject to any disclaimer, the term of this patent is extended or adjusted under 35 U.S.C. 154(b) by 0 days.

(21) Appl. No.: 17/258,758

(22) PCT Filed: Jul. 9, 2019

(86) PCT No.: PCT/EP2019/068324
§ 371 (c)(1),
(2) Date: Jan. 8, 2021

(87) PCT Pub. No.: WO2020/011746
PCT Pub. Date: Jan. 16, 2020

(65) Prior Publication Data
US 2021/0121556 A1    Apr. 29, 2021

(30) Foreign Application Priority Data

Jul. 9, 2018 (EP) ..................................... 18305906
Jul. 9, 2018 (EP) ..................................... 18305907

(51) Int. Cl.
| | | |
|---|---|---|
| *A61K 39/09* | (2006.01) | |
| *A61K 9/00* | (2006.01) | |
| *A61K 9/70* | (2006.01) | |
| *A61K 39/02* | (2006.01) | |
| *A61P 31/04* | (2006.01) | |
| *A61K 39/00* | (2006.01) | |

(52) U.S. Cl.
CPC .......... *A61K 39/099* (2013.01); *A61K 9/0014* (2013.01); *A61K 9/7023* (2013.01); *A61P 31/04* (2018.01); *A61K 2039/522* (2013.01); *A61K 2039/575* (2013.01); *A61K 2039/6037* (2013.01)

(58) Field of Classification Search
None
See application file for complete search history.

(56) References Cited

U.S. PATENT DOCUMENTS

| | | | |
|---|---|---|---|
| 8,287,899 B2 * | 10/2012 | Dupont | ............. A61F 13/00987 424/443 |
| 2001/0050083 A1 | 12/2001 | Marchitto et al. | |
| 2004/0258703 A1 | 12/2004 | Glenn et al. | |
| 2009/0143724 A1 | 6/2009 | Cormier et al. | |
| 2016/0015952 A1 | 1/2016 | Omachi et al. | |
| 2016/0263208 A1 | 9/2016 | Skountzou et al. | |

FOREIGN PATENT DOCUMENTS

| | | | | |
|---|---|---|---|---|
| WO | WO-2014155294 A1 * | 10/2014 | ......... | A61K 39/0018 |
| WO | WO-2016169971 A1 * | 10/2016 | ......... | C07K 16/2866 |

OTHER PUBLICATIONS

Kalach et al. J Allergy Clin Immunol, 116 (2005) pp. 1321-1326.*
Kashiwagi et al.J Vaccines Vaccin. Feb. 7, 2016(1):1-11.*
Buasri, W. et al. "Construction of Bordetella pertussis strains with enhanced production of genetically-inactivated Pertussis Toxin and Pertactin by unmarked allelic exchange" *BMC Microbiology*, 2012, pp. 1-16, vol. 12, No. 61.
Chen, X. et al. "Micro-fractional epidermal powder delivery for improved skin vaccination" *Journal of Controlled Release*, 2014, pp. 310-316, vol. 192.
Chen, X. et al. "Micro-fractional epidermal powder delivery for improved skin vaccination" *Journal of Controlled Release*, Oct. 28, 2014, pp. 1-22.
Gavillet, B. M. et al. "Needle-free and adjuvant-free epicutaneous boosting of pertussis immunity: Preclinical proof of concept" *Vaccine*, 2015, pp. 3450-3455, vol. 33, No. 30.
Pearson, F. E. et al. "Dry-Coated Live Viral Vector Vaccines Delivered by Nanopatch Microprojections Retain Long-Term Thermostability and Induce Transgene-Specific T Cell Responses in Mice" *PLoS*, Jul. 9, 2013, pp. 1-10, vol. 8, Issue 7, e67888.
Written Opinion in International Application No. PCT/EP2019/068324, dated Sep. 25, 2019, pp. 1-8.

* cited by examiner

*Primary Examiner* — Oluwatosin A Ogunbiyi
(74) *Attorney, Agent, or Firm* — SALIWANCHIK, LLOYD & EISNSCHENK (57) ABSTRACT

The present invention relates to improved epicutaneous administration methods for vaccination of a subject. In particular, the present invention discloses the use of an antigen for epicutaneous immunization, wherein the antigen is administered by epicutaneous application with a skin patch device in combination with an epidermal skin treatment.

21 Claims, 4 Drawing Sheets

| Site | Patient info | Method | Stratum Corneum Mean thickness (µm) | Stratum Corneum SD | Viable Epidermis Mean thickness (µm) | Viable Epidermis SD | References |
|---|---|---|---|---|---|---|---|
| Abdomen | Female – 36 ± 7.8 years old | Histology sectioning | 17.07 | 4.56 | 99.80 | 49.29 | Wei, Scientific report, 2017 |
| Forearm dorsal | Female – 47-63 years old | Histology sectioning | 13.20 | 2.30 | 59.90 | 6.70 | Khiao In, Anatomia Histologia Embryologia, 2019 |
|  | Male and Female – 20-68 years old | Histology sectioning | 18.30 | 4.60 | 56.60 | 11.50 | Sandby-Moller, Acta Derm Venereol, 2003 |
| Volar forearm | Male and Female – 18-54 years old | Confocal Raman Spectroscopy | 19.50 | 2.80 | N/A | N/A | Böhling, Skin Research and Technology, 2014 |
|  | Male and Female – 28-50 years old | Confocal Raman Spectroscopy | 18.00 | 3.90 | N/A | N/A | Crowther, British Journal of Dermatology, 2008 |
|  | Male and Female – 23-76 years old | Confocal Raman Spectroscopy | 13.60 | 4.33 | N/A | N/A | Egawa, Acta Derm Venereol, 2007 |
| Forearm | Female – 30-39 years old | Confocal Raman Spectroscopy | 21.30 | 2.60 | N/A | N/A | Lee, Skin Research and Technology, 2018 |
| Upper arm | Male and Female – 23-76 years old | Confocal Raman Spectroscopy | 21.80 | 3.63 | N/A | N/A | Egawa, Acta Derm Venereol, 2007 |
| Shoulder | Male and Female – 20-68 years old | Histology sectioning | 11.00 | 2.20 | 70.30 | 13.60 | Sandby-Moller, Acta Derm Venereol, 2003 |
| Buttock | Male and Female – 20-68 years old | Histology sectioning | 14.90 | 3.40 | 81.50 | 15.70 | Sandby-Moller, Acta Derm Venereol, 2003 |
|  | Male and Female – 5-75 years old | Histology sectioning | 13.40 | 3.80 | 70.60 | 12.60 | Therkildsen, Skin Research and Technology, 1998 |
|  | Male and Female – 18-54 years old | Confocal Raman Spectroscopy | 12.80 | 1.50 | N/A | N/A | Böhling, Skin Research and Technology, 2014 |
| Cheek | Male and Female – 28-50 years old | Confocal Raman Spectroscopy | 13.80 | 0.90 | N/A | N/A | Crowther, British Journal of Dermatology, 2008 |
|  | Male and Female – 23-76 years old | Confocal Raman Spectroscopy | 16.80 | 2.84 | N/A | N/A | Egawa, Acta Derm Venereol, 2007 |
| Lower leg | Male and Female – 18-54 years old | Confocal Raman Spectroscopy | 22.40 | 2.20 | N/A | N/A | Böhling, Skin Research and Technology, 2014 |
| Leg | Male and Female – 28-50 years old | Confocal Raman Spectroscopy | 13.00 | 6.90 | N/A | N/A | Crowther, British Journal of Dermatology, 2008 |
| Thigh | Male and Female – 15-31 years old | Histology sectioning | 10.90 | 3.10 | N/A | N/A | Holbrook, Journal of Investigative Dermatology, 1974 |
| Back | Male and Female – 25-31 years old | Histology sectioning | 9.40 | 2.20 | N/A | N/A | Holbrook, Journal of Investigative Dermatology, 1974 |

Figure 4

OPTIMIZED EPICUTANEOUS VACCINATION

CROSS-REFERENCE TO RELATED APPLICATION

This application is the U.S. national stage application of International Patent Application No. PCT/EP2019/068324, filed Jul. 9, 2019.

FIELD OF THE INVENTION

The present invention relates to improved epicutaneous administration methods for vaccination of a subject. In particular, the present invention discloses immunotherapeutic methods wherein an antigen is administered to a subject by epicutaneous route with a skin patch in combination with skin micro-perforation.

BACKGROUND OF THE INVENTION

Epicutaneous administration is a method of antigen delivery to the skin of a subject, which can stimulate an immune response in said subject.

Vaccination is a method of generating a protective immune response against a selected pathogen. Vaccination may be preventive, i.e., conducted prior to a subject's exposure to the pathogen, or curative, i.e., conducted after exposure, in order to increase, expand or stimulate the subject's immune defense against the pathogenic agent. Conventional vaccination comprises the parenteral, nasal or oral administration of an antigen to a subject. Most vaccination programs comprise the (repeated) parenteral administration (e.g. injection) to a subject of a selected antigen specific of the pathogen, thereby inducing or amplifying the subject's immune system against the pathogen. Conventional vaccination may also be oral or nasal. Topical applications of vaccine formulations on the skin have also been proposed, e.g., Mishra et al., 2006, which concerns a system of transcutaneous immunization using a liquid, vesicular, non-occlusive system with an adjuvant. Vaccination generally comprises a repeated administration protocol, including a priming administration followed by one or several boost administrations. In most cases, such a prime-boost vaccination, requiring more than a single immunization, is performed using the same vaccines multiple times as homologous boosts. Also, in conventional vaccination programs, the antigen is generally used in combination with one or more adjuvants, in order to generate the appropriate immune response.

*Bordetella pertussis* is a gram-negative coccobacillus which is the causative agent of pertussis, also called whooping cough. Until the introduction of a successful vaccine in the 1940s, whooping cough was a common illness in young children worldwide and a major cause of childhood mortality. Subsequent widespread vaccination resulted in a significant decrease in the number of cases worldwide. However, in recent years, the number of reported cases has been rising, mostly in countries using acellular pertussis vaccine. The emergence of pertussis infections may be due to an insufficient vaccination coverage and failure to reduce *B. pertussis* carriage, in particular, in adult population. Vaccination against pertussis is typically performed by injection, the pertussis antigen being combined with adjuvant. However, such injectable vaccines often lead to pain and to stress due to needle phobia and/or anxiety about potential adverse effects in particular due to the coadministration of the antigen with certain adjuvants. The administration by injection and the use of adjuvant are major contributors to vaccine refusal, which is becoming a global public health issue.

On the other hand, the route of antigen administration can play a key role in the development of active immunity, and the potential of epicutaneous administration has been investigated. For example, WO2007/122226 proposes the use of a dermal patch to obtain an immune reaction against antigens or allergens. The patch described in WO2007/122226 forms a chamber when applied to the skin of a subject, allowing a release of the biologically active substance through moistening. WO2009/080933 proposes a method enabling the induction of an antigen-specific immune response via epicutaneous route, without the need to use an adjuvant or to pre-treat or perforate the skin. WO2011/128430 describes a method combining a conventional parenteral priming and epicutaneous boosting, resulting in a strong and Th1-oriented immune response.

Despite the above strategies, there is still a need for optimized strategies for administering an antigen in the context of vaccination, including for performing vaccination against *Bordetella pertussis*.

SUMMARY OF THE INVENTION

The invention relates to the use of an antigen in an immunotherapeutic treatment of a disorder in a subject, wherein the antigen is administered to the subject by epicutaneous route, by means of a skin patch in combination with skin micro-perforation (also called herein skin microporation) at the site of application of said skin patch. The antigen may be from a pathogen, whereby the antigen is for vaccinating the subject against said pathogen. Typically, skin micro-perforation is performed so as to form one or more micropores (also called herein microperforations) on the skin, said micropores extending from the surface of the skin through one or several epidermis layers, but without extending into the dermis. Preferably, skin micro-perforation does not alter the basal layer of the epidermis. The micropores may have a depth of less than 150 µm, preferably from 5 µm to 100 µm and/or a diameter of at most 200 µm, preferably from 5 µm to 150 µm. The skin micro-perforation may be performed prior to, or simultaneously with, the administration of the antigen by means of the skin patch. Skin micro-perforation may be performed by means of laser microporator or by means of a mechanical micro-perforator. For instance, skin micro-perforation may be performed with a laser microporator, preferably with the following settings:

Laser source: Er:YAG of 2940 nm,
Fluence of at most 16 J/cm$^2$,
Number of pulses: from 1 to 3,
Pulse duration from 15 µs to 100 µs, preferably from 50 µs to 100 µs.

In some embodiments, the skin patch is occlusive and comprises a backing suitable to create with the skin a hermetically closed chamber, and wherein the antigen is deposited on the skin facing side of said backing, in dry form, preferably without any adjuvant, and optionally in combination with one or several pharmaceutically acceptable excipients.

The subject may be a primed human in need of a boosting vaccination against the pathogen. Alternatively, the vaccination may be for priming an immune response against the pathogen in the subject. The administration of the antigen by epicutaneous route, by means of a skin patch in combination with skin micro-perforation, may be repeated.

In some embodiments, the vaccination against the pathogen comprises:
- a step of priming an immune response against the pathogen and
- one or several steps of boosting said immune response, wherein at least one of the boosting steps comprises the administration of the antigen to the subject by epicutaneous route, by means of a skin patch in combination with skin micro-perforation at the site of application of said skin patch in the subject.

In some embodiments, the antigen is selected from the group consisting of viral antigens such as viral surface antigens, bacterial antigens such as bacterial adherence factors, bacterial virulence factors, outer-membrane proteins, immunogenic variants and fragments thereof.

The invention also relates to the use of a *Bordetella* antigen in the vaccination of a subject against *Bordetella*, wherein the antigen is administered by epicutaneous route by means of a skin patch in combination with skin micro-perforation at the site of application of said skin patch in the subject. Said use can be implemented as described above.

The antigen may be a detoxified pertussis toxin (PT), preferably a genetically detoxified recombinant PT comprising the mutations Arg9→Lys9 and Glu129→Gly129 in subunit S1 as compared to the sequence of wildtype PT.

In some embodiments, the subject is a primed adult or teenager in need of a boosting vaccination against pertussis.

A further object of the invention is the use of an antigen in the manufacture of a vaccine, wherein the vaccine is to be administered by epicutaneous route by means of a skin patch in combination with skin micro-perforation at the site of application of said skin patch in the subject. Said antigen may be from a pathogen, preferably from *Bordetella* and the vaccine may be for providing vaccination in a subject against a pathogen infection, such as pertussis, preferably boosting vaccination in a primed subject. Typically, the skin micro-poration and/or the skin patch are as defined above.

LEGEND TO THE FIGURES

FIGS. 1B and 1C show the impact of epidermis-limited skin micro-perforation on antigen uptake by skin DC. Skin samples were collected, and skin cells were isolated and labelled with the following antibodies for the analysis of antigen uptake by each of skin DC subsets: anti-Epcam-PE (Miltenyi Biotec, clone caa7-9G8), anti-CD11b-PerCP-Vio700 (Miltenyi Biotec, clone REA592), anti-CD11c-APC-Cy7 (BD Biosciences, clone HL3), anti-MHCII-VioBlue (Miltenyi Biotec, clone M5/114.15.2), anti-XCR1-VioBright FITC (Miltenyi Biotec, clone REA707). The percentage of OVA-positive (AF-647-positive) cells (B) and the median of OVA-AF647 fluorescence intensity (MFI) (C) were measured among OVA-positive cells in each DC subsets. Analyses were done for both naïve and OVA-primed mice, as indicated (n=8 per experimental group). Median and interquartile range are shown. P values were determined according to the Mann-Whitney test (*, P<0.05; , P<0.01; *, P<0.001; n.s., non-significant).

FIG. 3 shows the Study design for the evaluation of the impact of skin micro-perforation on the level of the specific humoral response induced by epicutaneous boost immunization. BALB/c mice were divided into two sets of 4 and 5 groups. The first set was primed using Viaskin® patches loaded with 25 μg of rPT and boosted twice at one-week interval using the same patches (prime/boost immunization). Before each Viaskin® application, mice were treated, or not, by skin laser micro-perforation. As a negative control, mice received 3 Viaskin® patches loaded with excipient (PBS) and, as a positive control, mice received a single injection of Boostrix (1.6 μg of chemically detoxified pertussis toxin, GSK) by intramuscular route. The second set of mice received an adoptive transfer of memory splenocytes isolated from Infanrix-immunized mice. These recipient mice were boosted one week after adoptive transfer with one application of Viaskin® loaded with 5 or 25 μg of rPT after, or not, skin laser micro-perforation treatment. As a negative control, mice received one Viaskin® patches loaded with excipient (PBS) and as a positive control, mice were boosted with a single injection of Boostrix (1.6 μg of chemically detoxified pertussis toxin, GSK) by intramuscular route. Blood samples were collected at day 30 for the first set of mice and at day 65 for the second set of mice, for the measurement of PT-specific antibody titers by ELISA.

DETAILED DESCRIPTION OF THE INVENTION

The present invention provides new improved epicutaneous administration methods and uses thereof. More specifically, the present invention relates to optimized administration of an antigen by epicutaneous application in combination with skin micro-perforation, for providing immunotherapy, such as vaccination, to a subject. In other words, the present invention relates to micro-perforation-assisted epicutaneous immunotherapy.

The Invention shows that skin micro-perforation strongly enhances or improves the immune response when combined with epicutaneous delivery of an antigen, for instance by means of an occlusive skin patch such as Viaskin®.

Surprisingly, the Inventors showed that minimally and epidermis-limited skin micro-perforation potentiates the immune response resulting from the epicutaneous administration of an antigenic compound.

As illustrated in the example section, laser micro-perforation with "soft settings" (namely enabling the targeting of the upper layers of epidermis only) was shown to increase the delivery of an antigen by epicutaneous route in BALB/c mice. An increase of ovalbumin antigen uptake by skin dendritic cells was also observed in mice treated by laser micro-perforation combined with patch application as compared to mice treated with skin patch application alone. Noteworthy, the Inventors showed that epidermis-limited skin micro-perforation enables to enhance the proportion of ovalbumin (OVA)-positive LC and cDC1 in the skin and the level of LC activation, as well as the number of OVA-positive DC in skin-draining lymph nodes following epicutaneous immunization. In line with these results, it was also shown that skin micro-perforation strongly increases OVA-specific immunity upon primary immunizations using Viaskin®-OVA.

Altogether these results demonstrate that epidermal micro-perforation potentiates immune response resulting from epicutaneous application of an antigen.

The Inventors confirmed that epidermal micro-perforation can potentiate epicutaneous administration of antigen in the context of vaccination against *Bordetella pertussis*. More precisely, the Inventors showed that the combination of skin micro-perforation with epicutaneous administration of a *B. pertussis* antigen remarkably improves the humoral response, as compared to epicutaneous vaccination alone or to conventional intramuscular vaccination in naïve and Infanrix®-primed mice. As illustrated in Example 4, the Inventors showed that skin micro-perforation enhanced antibody responses induced by epicutaneous vaccination in mice, using a prime/boost immunization scheme. Moreover, antibody titers induced were higher than those induced by a single intramuscular injection of the commercial *B. pertussis* boost vaccine (Boostrix). The increase in antibody response was also observed in Infanrix®-Hexa-primed mice boosted with the combination of skin micro-perforation and epicutaneous vaccination as compared with primed mice boosted epicutaneously without skin micro-perforation. Noteworthy, skin micro-perforation further allowed a reduction of the dose of antigen loaded onto Viaskin® by 5 folds, without impairing the magnitude of antibody response in primed mice. Accordingly, skin micro-perforation was shown to potentiate the immune response induced by epicutaneous administration of a *Bordetella* antigen.

As shown in Example 5, the Inventors further conducted a phase I clinical study to evaluate the safety and the immunogenicity of a booster vaccination using Viaskin® patches comprising a *Bordetella* antigen in combination with epidermal skin micro-perforation. The study was conducted in young adults and compared to boosting vaccination performed with Viaskin® patches without micro-perforation. The results demonstrate that vaccination with Viaskin® combined with skin micro-perforation was well-tolerated by the patients. Furthermore, skin epidermal micro-perforation was shown to potentiate the immune response induced by Viaskin® alone. 100% of the patients were seroconverted after the second boosting treatment with the combination of skin micro-perforation and Viaskin®, whereas boosting vaccination with Viaskin® alone induced seroconversion in 13.3% of the subjects. A significant increase in antigen-specific IgG titers was also observed in the group treated with micro-perforation in combination with Viaskin®.

The present invention thus shows, unexpectedly, that epidermis-limited skin micro-perforation enhances antibody responses induced by Viaskin® booster vaccination in humans. Importantly, antibody titers measured in human subjects who received Viaskin® associated with micro-perforation were within the same range than those induced by the commercial Boostrix® vaccine, which demonstrates the efficacy of the combination of epidermis-limited skin micro-perforation with epicutaneous delivery of *Bordetella* antigen in the context of pertussis vaccination.

The present invention thus discloses new vaccination strategies based on the combination of epidermal skin micro-perforation and epicutaneous administration.

The invention particularly relates to the use of an antigen from a pathogen in an immunotherapeutic treatment of a disorder in a subject, wherein the antigen is administered by epicutaneous route, by means of a skin patch in combination with skin micro-perforation at the site of application of said skin patch on the subject.

The invention also relates to the use of an antigen in an immunotherapeutic treatment of a disorder in a subject, which comprises:
  micro-perforating an area of the skin of the subject, and
  epicutaneously administering the antigen on said area of the skin, preferably by means of a skin patch.

The invention also relates to a method for providing an immunotherapeutic treatment of a disorder to a subject with an antigen, wherein said method comprises:
  micro-perforating an area of the skin of the subject, and
  epicutaneously administering the antigen on said area of the skin, preferably by means of a skin patch.

As described below, the antigen may be of any type and encompass antigens from tumor cells and antigens from pathogens.

In some embodiments, the invention is for providing vaccination to a subject in need thereof against a pathogen.

The invention also relates to an antigen from a pathogen (e.g. belonging to *Bordetella* genus such as *B. pertussis*) for use for vaccinating a subject against said pathogen, wherein the antigen is administered to the subject by epicutaneous route, by means of a skin patch device in combination with skin micro-perforation at the site of application of said skin patch.

The invention also relates to an antigen from a pathogen (e.g. a *Bordetella* pathogen) for use in inducing or priming an immune response against said pathogen or for amplifying a pre-existing immune response against said pathogen in a subject, wherein the antigen is administered by epicutaneous route, by means of a skin patch in combination with skin micro-perforation at the site of application of said skin patch.

A further object of the invention relates to an antigen from a pathogen (e.g. belonging to *Bordetella* genus such as *B. pertussis*) for use in a method for vaccinating a subject against said pathogen, which comprises:

micro-perforating an area of the skin of the subject, and
epicutaneously administering the antigen on said area of the skin of the subject, preferably by means of a skin patch device.

The micro-perforation of the skin may be performed before, preferably immediately prior to, or simultaneously with, the administration of the antigen of interest by epicutaneous route. As fully explained further below, skin micro-perforation is performed so as to alter one or several epidermis layers while essentially maintaining integrity of the dermis and hypoderm. Preferably, the depth of micropores generated by skin micro-perforation does not extend to the basal layer of epidermis.

The invention may be used to improve, induce, reinforce, expand and/or repolarize an immune response, to target a specific group of dendritic cells, or to produce immunity to, e.g. immunize against any pathogen. The invention can also be used to treat (e.g. present, delay, reduce, avoid, eliminate) any disease and/or disorder in particular caused by a pathogen. In some embodiments, the pathogen belongs to *Bordetella* genus.

The invention further relates to the use of an antigen from a pathogen (e.g. a *Bordetella* pathogen) for the manufacture of a composition for vaccinating a subject against said pathogen, by epicutaneous route, by means of a skin patch device in combination with skin micro-perforation at the site of application of said skin patch.

A further object of the invention is a kit for providing an immunotherapeutic treatment of a disorder in a subject, which comprises:

one or several skin patches comprising an antigen (e.g. a *Bordetella* antigen), and
means to perform skin micro-perforation at the site of application of the patch in the subject, preferably a laser microporator (also called herein micro-perforator) or a mechanical micro-perforator (also called herein mechanical microporator), as described further below.

The present disclosure will be best understood by reference to the following definitions:

Definitions

As used therein, "epicutaneous administration or application" designates the application of a compound on a surface of the skin of a subject under conditions allowing a contact with the surface of the skin. Epicutaneous administration typically comprises skin application under condition sufficient to allow penetration or diffusion of the compound in the superficial layer(s) of the skin, preferably in the epidermis layers, and/or contact of said compound with immune cells.

As used herein, "Epidermis" refers to the outer layer of the skin, the inner layers being the dermis and hypodermis. The epidermis is composed of 4 or 5 layers depending on the region of the skin being considered. These layers, in descending order, are the *stratum corneum*, the *stratum lucidum*, the *stratum granulosum*, the *stratum spinosum* and the *stratum basale*.

Figure 4:
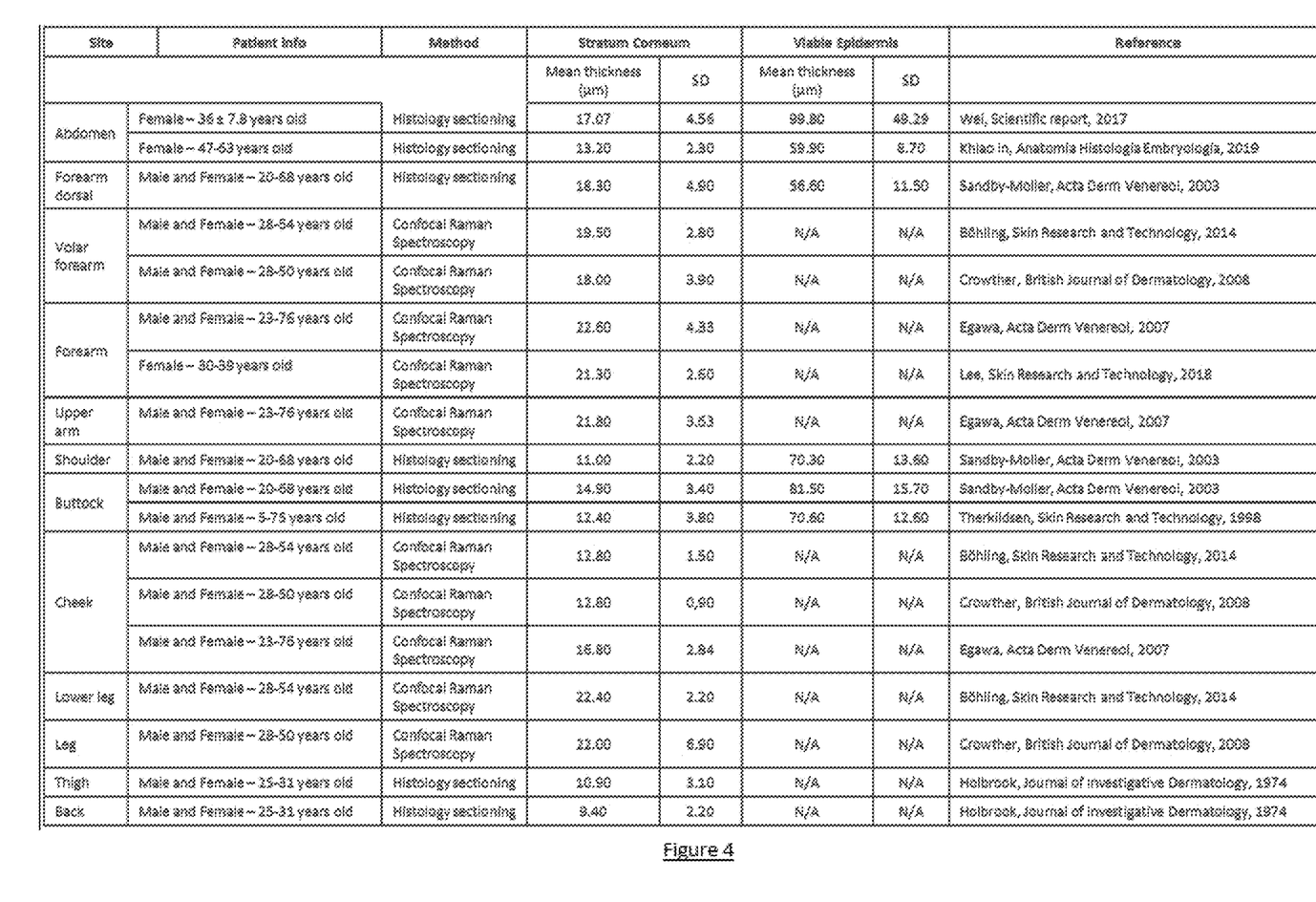
FIG. 4 shows the mean thickness of *Stratum corneum* and epidermis in Human, depending on the body site and the age of the subject. These data have been collected from the scientific literature.

The *stratum corneum* is mostly composed of corneocytes which correspond to keratinocytes in their last stage of differentiation. The *stratum corneum* has a thickness generally ranging from about 5 to 50 µm, e.g. 10 to 40 µm depending on the location of the skin and the age of the subject. Generally, the mean thickness of *stratum corneum* is from about 9 µm to 30 µm as illustrated in the table of FIG. 4 in adults and in body site such as arms, legs, shoulders, back or abdomen.

As used herein, "skin micro-perforation" refers to a process aiming at forming at least one, preferably a plurality of, micropores, micro-perforations, micro-punctures, or micro-channels of a desired depth in the skin. Typically, skin micro-perforation forms an array of microperforations (also referred to micropores herein) at the surface of the skin. Skin micro-perforation can be performed by the means of microperforator (also known as microporator) devices or external physical treatments such as laser and electroporation. Microperforations refer to superficial, small, holes, punctures, pores, or perforations in the skin having preferably at least 1 µm in depth and at least 1 µm in diameter. Preferred sizes of micro-perforations are described further below. In some particular embodiments, the micro-perforations extend from the surface of the skin through the *stratum corneum*, and optionally through the upper layers of the epidermis, but without extending to the basal layer of the epidermis and the dermis. In some embodiments, the micro-perforations are organized as an array.

As used herein, the terms "microperforation" and "micropores" are synonymous and thus interchangeable. The same applies for "micro-perforation" and "microporation".

As used herein, "epidermal skin micro-perforation", "epidermis-limited micro-perforation", "epidermal skin microporation" or epidermis-limited microporation" refers to skin micro-perforation (or skin microporation) wherein the microperforations (or micropores) extend from the surface of the skin through one or several epidermis layers, but without extending into the dermis. As mentioned above, in preferred embodiments of "epidermal skin micro-perforation", the micropores do not extend into the basal layer of the epidermis.

As described herein, "immunotherapy or immunotherapeutic treatment" refers to a treatment wherein a desired immune reaction is induced in a patient in order to improve his/her condition. Immunotherapeutic treatment encompasses the treatment and/or the prevention of a disorder in the subject. As used herein, a disorder encompasses any disorder or disease caused by a pathogen or resulting from an infection by the pathogen in the patient.

As described herein, the term "vaccination" or "vaccinating" designates typically the administration of one or more antigens to a subject, to produce and/or enhance an immune response against the antigen(s).

The antigen may be endogenous and may refer to a protein abnormally and/or solely expressed by tumor cells in the subject. In such a case, the vaccination refers to antitumor immunotherapy.

Alternatively, the antigen may derive from a pathogen. The vaccination may be useful to treat or prevent (e.g. delay, reduce, avoid, eliminate) a disorder caused by the pathogen or resulting from an infection by the pathogen in the subject.

The administration of the antigen can be sequential and can typically include a priming immunization followed by one or several boosting immunizations.

The term "vaccination" encompasses (i) priming vaccination wherein the antigen is administered in a naïve subject in order to induce an immune response in said subject, (ii) boosting vaccination wherein the antigen is administered to boost, namely amplify a pre-existing immune response in the subject as well as (iii) priming/boosting vaccination wherein the antigen is first administered to induce an immune response, and then administered again to boost the resulting immune response.

Within the context of the present invention, the term "pathogen" refers to any agent that can cause a pathological condition. Examples of "pathogens" include, without limitation, cells (e.g., bacteria cells, diseased mammal cells, cancer mammal cells), fungus, parasites, viruses, prions or toxins. Preferred pathogens are infectious pathogens. In a particular embodiment, the infectious pathogen is a virus, such as hepatitis virus, rotavirus, chicken pox virus, influenza, cytomegalovirus, flu, HIV, Ebola virus, or Rabies. Specific examples of infectious pathogens include, without limitation, *C. diphteriae, C. tetani, B. Pertussis*, Poliovirus, Mumps, Rubella, Varicella (Chicken pox), *Streptococcus pneumoniae*, Rotavirus, HPV (Human Papillomavirus), African trypanosomiasis (sleeping sickness), Anthrax, Avian influenza ("bird flu"), Buruli ulcer disease, Cholera, Crimean-Congo haemorrhagic fever, Dengue and dengue haemorrhagic fever, Ebola haemorrhagic fever, Enteroviruses—non polio, *Haemophilus influenzae* type B (HiB), Hendra virus, Hepatitis A, Hepatitis B, Hepatitis C, Hepatitis D, Hepatitis E, Influenza (Seasonal), Lassa fever, Legionellosis, Leprosy, Malaria, Marburg haemorrhagic fever, Measles, Meningococcal meningitis, Nipah virus, Plague, Poliomyelitis, Rift Valley fever, Smallpox, Tuberculosis or Yellow fever pathogen.

In some embodiments, the antigen is from a *Bordetella* antigen. Accordingly, the method of the invention may be for vaccinating the subject against a *Bordetella* infection such as pertussis.

"*Bordetella*" or "*Bordetella* pathogen" refers to any pathogen belonging to *Bordetella* genus which can infect a subject, preferably a mammal and more preferably a human. *Bordetella* species of interest encompass, without being limited to, *Bordetella bronchiseptica, Bordetella holmesii Bordetella parapertussis, Bordetella bronchialis, Bordetella flabilis, Bordetella sputigena* and *Bordetella pertussis*.

"*Bordetella* infection" refers to any infection caused by a bacterium belonging to *Bordetella* genus in a subject, preferably a mammal. The site of infection is preferably the respiratory tract. In preferred embodiments, the subject is a human. In that case, the *Bordetella* pathogen may be selected, without limitation, from *Bordetella bronchiseptica, Bordetella holmesii Bordetella parapertussis, Bordetella bronchialis, Bordetella flabilis, Bordetella sputigena* and *Bordetella pertussis*. In some embodiments, the *Bordetella* infection is pertussis, also called whopping cough, which is typically caused by *Bordetella parapertussis* and/or *Bordetella pertussis*. In a particular embodiment, the *Bordetella* infection is pertussis and the causal pathogen is or includes, for instance, *Bordetella pertussis*.

An "antigen", as used therein, designates any molecule or substance which can cause a T-cell or B-cell immune response in a subject. An antigen specific for a pathogen is, typically, an element obtained or derived from said pathogen, which contains an epitope, and which can cause an immune response against the pathogen. Depending on the pathogenic agent, the antigen may be of various nature, such as a (poly)peptide, protein, nucleic acid, lipid, cell, etc. Live weakened forms of pathogens (e.g., bacteria, viruses), or killed or inactivated forms thereof may be used as well as antigens as well as purified material therefrom such as proteins, peptides, lipids, etc. The antigen may be naturally occurring or artificially created. It may be exogenous to the treated mammal, or endogenous. The antigen may be produced by techniques known per se in the art, such as for instance synthetic or recombinant technologies, or enzymatic approaches. Specific examples of antigens suitable for use in the present invention include viral antigens, preferably viral surface antigens, such as e.g., Hepatitis A, B or C virus antigen and bacterial antigens such as bacterial adherence factors, bacterial virulence factors, outer-membrane proteins, immunogenic variants and fragments thereof.

In a particular embodiment, the antigen is a protein, polypeptide and/or peptide. The terms "polypeptide", "peptide" and "protein" are used interchangeably herein to refer to a polymer of amino acid residues. The terms also apply to amino acid polymers in which one or more amino acid residues may be modified or non-naturally occurring residues, such as an artificial chemical mimetic of a corresponding naturally occurring amino acid. It should be understood that the term "protein" also includes fragments or variants of different antigens, such as epitope-containing fragments, or proteins obtained from a pathogen and subsequently enzymatically, chemically, mechanically or thermally modified. Typically, the protein used in vaccination is modified so as to significantly decrease and even annihilate its deleterious effects while keeping or increasing its immunogenicity. For instance, the antigen may be a chemically detoxified protein such as a toxoid or a genetically detoxified variant thereof.

As will be discussed further below, the antigen may be in various states, such as liquid or dry state. For skin application by means of an occlusive skin patch, the antigen is preferably in dry state.

In some embodiments, the antigen is a *Bordetella* antigen.

In the context of the invention, "*Bordetella* antigen" refers to an antigen specific for a *Bordetella* pathogen such as *Bordetella bronchiseptica, Bordetella holmesii, Bordetella parapertussis, Bordetella bronchialis, Bordetella flabilis, Bordetella sputigena* and *Bordetella pertussis*, preferably *Bordetella pertussis*. The antigen may be of various nature, such as a (poly)peptide, protein, nucleic acid, lipid, cell, etc. The antigen may also be a live weakened form, a killed form or an inactivated form of a *Bordetella* pathogen. In the context of the invention, the *Bordetella* antigen is preferably an acellular antigen of the protein-type. Typically, the *Bordetella* antigen maybe a protein expressed by a *Bordetella* pathogen which has been thermally, chemically or recombinantly modified so as to decrease or annihilate its deleterious effect (e.g. its enzymatic activity) and/or increasing its immunogenicity. For instance, the *Bordetella* antigen may be a toxoid, namely a pathogenic protein which have been subjected to a treatment selected from heat treatment, chemical treatment, e.g. with peroxide hydrogen, formaldehyde or glutaraldehyde, and/or fusion or conjugation treatment. Such treatments are typically performed to increase its immunogenicity while decreasing its deleterious biological activity. A fusion or conjugation treatment refers to a treatment wherein the protein or a fragment thereof is fused or conjugated to another entity, typically a carrier protein such as Keyhole limpet hemocyanin (KLH) or serum albumin. Alternatively, the antigen may be a pathogenic protein which has been genetically modified so as to be detoxified. A genetically detoxified recombinant protein refers to a mutant or variant comprising one or several mutations in its amino acid sequence as compared to the wild type pathogenic protein which induces a loss of pathogenic activity while maintaining immunogenicity. For instance, when the antigenic protein is an enzyme, said mutation(s) can be introduced in the catalytic site and/or the binding site of substrate so as to significantly decrease its enzymatic activity. In some embodiments, said variant may have been subjected to one or several additional detoxification treatments, for instance by means of chemical treatment or heat. Alternatively, the *Bordetella* antigen may be an antigenic fragment of a protein (which typically comprises an epitope) from a *Bordetella* antigen, which can be optionally coupled or fused with a carrier protein such as albumin or KLH. Several copies of said fragment can be coupled with the protein carrier, whereby the antigen is multivalent.

*Bordetella* antigens of interest encompass, without being limited to, adherence factors, virulence factors, outer-membrane proteins, immunogenic variants and fragments thereof. In some embodiments, the *Bordetella* antigen derives from *Bordetella pertussis* and is preferably selected from pertussis toxin (PT), filamentous hemagglutinin, pertactin, fimbria, adenylate cyclase toxin, tracheal cytotoxin, variants thereof, fragments thereof, detoxified forms thereof and combinations thereof.

In a preferred embodiment, the *Bordetella* antigen is selected from pertussis toxin (PT), filamentous hemagglutinin, pertactin, and combinations thereof, preferably in a detoxified form.

In a particular embodiment, the *Bordetella* antigen is a detoxified pertussis toxin from *Bordetella pertussis*. Said detoxified pertussis toxin may be obtained recombinantly and/or by subjecting the native toxin to chemical and/or heat treatment. In a preferred embodiment, the *Bordetella* antigen is a genetically detoxified recombinant pertussis toxin comprising mutations Arg9→Lys9 and Glu129→Gly129 (rPT-R9K/E129G) in subunit S1 as compared to the subunit S1 sequence of wildtype Pertussis toxin (see Buasri et al., 2012, the content of which being incorporated by reference). The production of such a *Bordetella* antigen is described in EP 2 802 646 in the name of BioNet, the content of which being incorporated by reference.

As will be discussed further below, the *Bordetella* antigen may be in various states, such as liquid or dry state. Typically, for skin application(s), the antigen is in dry state, while for conventional vaccination by intramuscular or subcutaneous route, the antigen is in liquid form.

As used herein, the "subject" refers to any subject in need of immunotherapeutic treatment of a disorder. The subject is preferably a mammal and more preferably a human. The patient may be of any gender and of any age. The subject may be a newborn, an infant, a child, a teenager, or an adult.

In some other embodiments, the subject is in need of a vaccination against a pathogen. The subject may be a pre-immunized adult, namely an adult who has been immunized against the pathogen preferably during his/her infanthood or childhood, whereby he/her has developed an immune response against the pathogen. Such subjects are in need of boosting vaccination, namely in need of a re-amplification of their pre-existing immune response against the pathogen. Alternatively, the subject may be naïve with respect to the pathogen, whereby said subject is in need of priming vaccination. In some embodiments, the subject is an adult, for instance of 18 to 90 years-old or 20 to 80 years-old.

In some embodiments, the subject is in need of vaccination against a *Bordetella* infection, preferably against pertussis. For instance, the subject may be a newborn or an infant, in particular in need of priming vaccination against pertussis. Alternatively, the subject may be an adult, in particular in need of boosting vaccination against pertussis. Typically, the subject may be a pre-immunized adult, namely an adult who has been immunized against pertussis preferably during his/her infanthood or childhood, whereby his/her has developed an immune response against pertussis.

Such subjects are in need of boosting vaccination, namely in need of a re-amplification of their pre-existing immune response against pertussis. In some embodiments, the subject is a young adult of 18 to 45 years old.

Skin Micro-Perforation

The invention relies on the combination of skin micro-perforation and epicutaneous administration of an antigen, preferably by means of a skin patch.

Skin micro-perforation is performed on the site of application of the antigen. In preferred embodiments, the settings of the skin micro-perforation process are such that one or several epidermis cell layers are perforated while the integrity of the dermis and the hypoderm of the skin is essentially maintained, and even preserved. In some embodiments, skin micro-perforation is performed so as to create micropores into one or several upper layers of the epidermis, namely the *stratum corneum*, the *stratum granulosum*, and/or the *stratum spinosum*. In some embodiments, skin micro-perforation affects the *stratum corneum* and the *stratum granulosum* only. In other embodiments, the *stratum corneum* is the sole epidermis layer affected by skin micro-perforation. In some other or additional embodiments, the skin micro-perforation is performed so as to essentially maintain, and even preserve, the integrity of the basal layer of the epidermis.

Preferably, an area of the skin surface where epicutaneous application shall occur is prepared by epidermal micro-perforation. In a particular embodiment, epidermal micro-perforation is performed so that micropores extend from the surface of the skin into one or several epidermis layers but do not reach epidermis basal layer. In some further or additional embodiments, the micropores are limited to the *stratum corneum* and optionally can extend at least partially into the *stratum granulosum* and/or the *stratum spinosum*. Preferably, the micropores do not extend beyond the *stratum spinosum*. Micro-perforation can be performed in any area of the body skin such as shoulders, scapula, arms, and thighs.

The micro-perforation depth is determined in view of the subject, as epidermis thickness may vary depending on the body site and the individual features of the subject such as gender, age, pigmentation, or living habits. Skin micro-perforation may be performed so as to obtain an array of micropores on a skin area of the patient with micropore depth which does not reach the dermis, preferably which does not reach the basal layer of epidermis.

The thickness of the epidermis as well as that of epidermal cell layers are well-documented in the literature, especially for healthy skin, as shown in FIG. 4. FIG. 4 shows the variation of the thickness in *stratum corneum* and in the viable epidermis composed of *stratum* basale, *stratum spinosum, stratum granulosum* and *stratum lucidum* depending on the body site and the age of the subject. As shown in FIG. 4, for human adults, the thickness of the *stratum corneum* is generally from about 10 μm to about 25 μm, and that of the viable epidermis ranges from about 50 to about 100 μm. Thus, for a given subject, the skilled artisan is able to determine the micro-perforation depth enabling to cross the *stratum corneum* without extending into the dermis, based on the data collected in the literature. Alternatively, the skilled artisan can assess micro-perforation depth to perform in the subject by means of histology sectioning or by means of in vivo analysis e.g. by confocal Raman spectroscopy, confocal laser scanning microscopy or ultrasounds, at the body site to micro-perforate. For instance, one can use the confocal laser scanning microscope VivaScope® 1500 (Lucid® Inc.).

For human subject, preferably an adult subject, micro-perforation depth is typically less than 150 µm, preferably less than 130 µm, more preferably less than 120 µm and even more preferably less than 100 µm.

In some preferred embodiments, the skin micro-perforation is performed so as to obtain one or several micropores (also defined herein as microperforations), preferably an array of micropores, having a depth from 1 µm to 100 µm, preferably from 5 µm to 80 µm, for instance from 10 µm to 70 µm. A micropore depth from 5 µm to 80 µm encompasses a micropore depth from 5 µm to 10 µm, 10 µm to 15 µm, from 15 µm to 20 µm, from 20 µm to 25 µm, from 25 µm to 30 µm, from 30 µm to 35 µm, from 35 µm to 40 µm, from 45 µm to 50 µm, from 50 µm to 55 µm, from 55 µm to 60 µm, from 60 µm to 65 µm, from 65 µm to 70 µm, from 70 µm to 75 µm and from 75 µm to 80 µm.

As illustration, skin micro-perforation is performed so as to obtain micropores having a depth from about 40 µm to 80 µm. As a further illustration, skin micro-perforation is performed so as to obtain micropores having a depth from about 5 µm to 40 µm or from 5 µm to 20 µm.

The micropore diameter is typically of less than 200 µm. Accordingly, skin micro-perforation is typically performed so as to obtain micropores having a diameter from 5 µm to 150 µm, such as from 50 µm to 100 µm or from 5 µm to 50 µm.

The perforation density is typically from 1% to 30%, such as from 1% to 15%, 5% to 11% or from 7% to 9%. The micropore density refers to the ratio of "the number of micropores multiplied by the area of a single micropore" to 'the total area of the skin which have been treated by microporation", said ratio being multiplied by 100.

In some embodiments, the micro-perforated (or microporated) skin is characterized by an array of micropores having the following features:
 a perforation depth from 10 µm to 70 µm, and
 a perforation density from 5% to 11%.

In some embodiments, the micro-perforated surface of the skin almost corresponds to the surface of application of the patch. Accordingly, skin micro-perforation is typically performed so as to obtain an array of micropores having an area almost equal to the area of the skin patch.

Alternatively, the micro-perforated surface of the skin is smaller than the surface of application of the patch.

The size/form of the micro-perforated area on the skin surface may be adapted depending on the subject and patch device used. Preferably, the micro-perforated area is essentially similar or smaller than the application surface of the patch device.

Typically, the micro-perforated area may have a surface from 0.1 to 25 cm$^2$, for instance from 0.1 to 9 cm$^2$ or from 0.25 to 6.5 cm$^2$ such as 0.3 to 2.5 cm$^2$.

The micro-perforations may form an array on the skin. The array may have any form, such as square, circle, etc. The shape and the geometrical arrangement of micropores are typically defined by the settings of the device or system used to perform micro-perforation.

In a preferred embodiment, skin micro-perforation is performed on an intact area of the skin, namely on a healthy area of the skin. Thus, the site of micro-perforation is preferably devoid of any skin alteration such as redness, irritation, wound, or other inflammatory skin conditions e.g. eczema.

Skin micro-perforation can be performed prior to, or simultaneously with, the application of the antigen on the skin.

In some embodiments, skin micro-perforation is performed immediately before the application of the antigen. In some other embodiments, skin micro-perforation and the application of the skin patch device are performed simultaneously.

The skin micro-perforation can be performed by any methods known in the art, such as with a mechanical micro-perforator or external physical techniques e.g. by thermal ablation laser, radiofrequencies, electroporation, and low-frequency ultrasounds.

In some embodiments, skin micro-perforation is performed by the means of a laser, preferably a pulsed infrared laser such as $CO_2$ laser and erbium-doped yttrium aluminum garnet (Er:YAG) laser. Typically, such infrared lasers work on wavelengths of about 1 to 10 µm which induce vibrational excitation and heating of water molecules in very short time, leading to vaporization and ablation of surrounding tissue. In other words, with such lasers, micropores are created by thermal ablation of specific skin cell layers in micron-sized columns. Such lasers are known as fractional ablative lasers. Laser sources include Er:YAG, ER/Pr:YAG, pulse CO2, Ho:YAG, Er:YAP, Er/Cr:YSG, diode lasers, and the like.

In a preferred embodiment, an (Er:YAG) laser is used. For instance, one can use the technology Precise Laser Epidermal SystEm (P.L.E.A.S.E), developed by the company Pantec Biosolutions, or other similar devices available on the market.

In some embodiments, the skin micro-perforation is performed with an erbium-doped yttrium aluminum garnet (Er:YAG) laser micro-perforator. The wavelength of such a laser is 2.94 µm. The settings of the laser, in particular the fluence (i.e. the total energy delivered by cm$^2$), the number of pulses and the duration of the pulse are determined in view of the features of micro-perforations which are sought, the patient individual features and the body site of administration.

With an erbium-doped yttrium aluminum garnet (Er:YAG) laser micro-perforator and for a human subject, the fluence is generally less than 16 J/cm$^2$. The number of pulses by perforation may be from 1 to 3. Pulse duration may be from 15 µs to 100 µs.

For instance, one can perform skin micro-perforation in a human adult subject with a (Er:YAG) laser having the following settings:
 Fluence: 14.7 J/cm$^2$,
 Number of pulses: 3,
 Pulse duration: 75 µs.

With such settings, a micro-perforation array having a pore depth of around 60 µm can be obtained.

In another embodiment, the skin micro-perforation is performed with a mechanical micro-perforator. Mechanical micro-perforator devices may be useful to disrupt the *stratum corneum* layer of skin and then removed. Said devices are typically pressed against the skin in an effort to pierce the *stratum corneum* whereby an array of micropores is obtained within the epidermis of the subject.

A mechanical micro-perforator may comprise a planar substrate having thereon an array of sharp microrods or micro-pikes, also called microneedles. The microrods or micro-pikes may be in any elongated shape suitable for providing the skin piercing.

In particular, the tip portion of the microrods is designed to pierce the *stratum corneum* of the skin of a patient while providing minimal pain to the patient. For instance, the tip portion may have a pyramidal or triangular shape. The dimensions of the microrods as well as the geometry and the density of the microrod array vary depending on the skin microporation pattern which is sought. The microrods may be sufficiently long to penetrate through the *stratum corneum* layer and optionally through the *stratum lucidum*, the *stratum granulosum*, and the *stratum spinosum* while being sufficiently short to not penetrate the dermis and preferably enough short to not penetrate the basal layer of the epidermis as well.

Each microrod may have a length of about 5 μm to about 2000 μm. In addition, each microrod may have a width of about 5 μm to about 200 μm.

The substrate and the microrods are typically made of, or coated with, a biocompatible material. The microrods may be formed in the same material as, or in a material different, from that of the substrate. Representative materials include metals and alloys such as stainless steel, palladium, titanium, and aluminum; plastics, polycarbonate, polyetheretherketone, polyimide, polymethylpentene, polyvinylidene fluoride, polyphenylsulfone, polyethylene terephthalate (PET), polyethylene terephthalate-glycol modified (PETG), polyimide, polycarbonate; and ceramics.

In some embodiments, microporation may be performed simultaneously with the epicutaneous administration of the compound. In that case, the microrod array may be mounted within the adhesive occlusive patch. To allow the delivery of the compound from the patch into the epidermis, the substrate of the microrod array may comprise one or several apertures. Additionally or alternatively, at least one microrod may be hollow or comprise a transversal and elongated channel.

Mechanical micro-perforators are available on the market. For illustration, one can cite 3M microchannel skin system.

Epicutaneous Application of an Antigen According to the Invention

Epicutaneous application of the antigen is typically performed using a skin patch device, preferably an occlusive skin patch suitable to maintain contact between the antigen and the skin of the subject. The antigen can be present in pure form or as an admixture with pharmaceutical excipient(s), other antigen(s) and/or with adjuvant(s) in the patch.

In some embodiments, the skin micro-perforation is performed before the administration of the antigen. In that case, the skin patch is disposed onto the portion of skin in the patient which have been micro-perforated.

In some embodiments, the patch does not alter integrity of the skin. In a more preferred embodiment, the method of the invention uses a skin patch as described in international patent applications WO2002/071950 and WO 2007/122226.

The results presented in the application show that particularly advantageous immune response is produced when the epicutaneous application of an antigen is performed using an occlusive skin patch such as Viaskin®. Such a patch is occlusive and is configured to use said antigen in dry form. For instance, the antigen may be maintained on the inner surface of the patch in the absence of any adhesive, e.g. through electrostatic and/or Van der Waals forces.

The preparation and characteristics of the Viaskin® patch are disclosed in detail in the above quoted applications, which are incorporated herein in their entirety by reference.

In some embodiments of the invention, the antigen is applied on the skin using a patch, preferably an occlusive patch, comprising a support to which said antigen is deposed or bound. Preferably, said antigen is bound to the support of the patch e.g. without the mean of any adhesive and through electrostatic and/or Van der Waals forces. The support of the patch may be comprised of glass or polymer chosen from the group consisting of cellulose plastics (CA, CP), polyvinyl chloride (PVC), polypropylenes, polystyrenes, polyurethanes, polycarbonates, polyacrylics, polyolefines, polyesters such as PET, polyethylenes and ethylene vinyl acrylates (EVA).

For the performance of the present invention, on can use a patch comprising a backing adapted to create with the skin a hermetically closed chamber. This backing may have the dry antigen disposed on its skin facing side, e.g. in dry form. Upon application to the skin, moisture increases in the chamber, leading to antigen dissolution and contacting with the skin. In other words, when applied on the skin, the patch of the invention forms an occlusive chamber where the antigen, preferably in dry form, deposited on the inner surface of the chamber, is solubilized by trans-epidermal water loss and can then permeate the *stratum corneum* to the epidermal-dermal junction of the skin.

In some embodiments, the occlusive skin patch comprises a breathable over-adhesive, a backing preferably made of polyethylene terephthalate (PET) and an adhesive crown, the adhesive crown and the backing being adapted to create with the skin a hermetically closed chamber. Typically, the antigen is present in dry form onto the skin facing side of the backing. The antigen may have been deposed onto the backing by electrospray as described in WO2009095591.

In a preferred embodiment, the antigen is present in dry form in the patch. The antigen may be present in a dry composition, namely as a dry mixture with pharmaceutically excipient(s) and/or pharmaceutically adjuvant(s). In this regard, the term "dry" designates the fact that the antigen or the antigen-containing preparation is substantially powdered, e.g., in the form of particles which may be individualized or agglomerated.

Alternatively, the antigen may be in the form of a liquid composition and applied using known devices, such as occlusive devices having a reservoir or a perforated membrane.

In a preferred embodiment, the antigen is administered in dry form, optionally combined with one or several antigens or pharmaceutically excipients, and without any adjuvant such as aluminum hydroxide or aluminum potassium.

Pharmaceutically acceptable excipients that may be used are, in particular, described in the Handbook of Pharmaceuticals Excipients, American Pharmaceutical Association (Pharmaceutical Press; 6th revised edition, 2009). Examples of appropriate excipients include, but are not limited to, solvents such as water or water/ethanol mixtures, fillers, carriers, diluents, binders, osmotic agents, salts, buffering agents, stabilizers, antioxidants, preservatives, surfactants, wetting agents, and the like. For instance, the antigen may be formulated with one or several excipients selected from buffering agents, diluents, surfactants, and stabilizers. As illustration only, the antigen may be formulated in a liquid formulation (e.g. as an hydroalcoholic solution) comprising one or several excipients, said formulation being deposited, for instance sprayed, on the skin facing backing of the patch, whereby a solid deposit of the antigen together with the excipients is obtained.

Combination Treatment and Protocol

Skin micro-perforation may be performed prior to, or together with, application of the patch comprising the antigen, depending on the method used to perform micro-perforation.

When micro-perforation is performed first, the patch is applied before complete re-epithelization of the micropores. Preferably, the patch is applied on micro-perforated skin wherein the micropores have not been substantially re-epithelized and are thus at least partially open.

Typically, micro-perforation may be performed prior to application of the antigen by means of the skin patch, such as less than one hour before, preferably less than 30 min before, such as less than 20, 15, 10, or 5 minutes before. In some embodiments, micro-perforation is performed immediately prior to the application of the skin patch, which means that micro-perforation treatment is performed less than 5 minutes, such as less than 1 minute before the application of the patch.

In such embodiments, the skin patch is thus applied on pre-micro-perforated skin area.

Application of the patch on skin is typically performed under conditions and/or for a period of time sufficient to allow the antigen to penetrate into the *stratum corneum* of the epidermis and/or to reach immune cells.

For administration of the antigen, the duration of the patch application on the skin is preferably from 2 to 96 hours, such as from 5 h to 72 h. For a patch, such as a Viaskin®, the duration of contact is typically from 2 hours to 48 hours, such as from 2 h to 6 h, 6 h to 12 h, from 12 h to 24 h, from 24 h to 36 h and from 36 h to 48 h. The duration of skin patch application on skin can depend on the immunotherapeutic effect which is sought. e.g. the induction of an immune response or the enhancement of a pre-existing response. For instance, the patch can be applied on the skin during about 48 h.

The application of the antigen may be single or repeated, depending on the antigen, the subject and the type of immunotherapy which is sought. For instance, application may be repeated between 1 and 5 times, preferably 1, 2, 3, 4 times over a period of time which may extend from 1 day to several months, and even several years when the antigen is used in boosting vaccination.

Preferably, each application may be separated from another by 1 day to several weeks, typically by 1 week to 10 weeks.

In a particular embodiment, the method of the invention comprises from 1 to 5 patch applications of 6, 24, 36 or 48 hours, during 1, 2, 3 or 4 weeks.

If the antigen application is repeated, the micro-perforation treatment is preferably repeated prior to, or together with, each application of said antigen, or most of said applications. The setting of the micro-perforation process can be the same or can change at each/some application.

In a specific embodiment, in particular in the context of boosting vaccination against pertussis, the combination of skin micro-perforation and skin patch is repeated at least 2 times, for instance 2, 3 or 4 times, at 1-, 2-, 3-, or 4-week interval. For instance, the application of the skin patch is repeated once, at a 2-week interval, and skin micro-perforation is performed prior to, or simultaneously with, each application of the patch.

Vaccination

As mentioned above, the immunotherapeutic treatment of the invention encompasses vaccination, preferably vaccination against a pathogen.

Thus, in some embodiments, the antigen is specific for a pathogen and is used for vaccinating a subject against said pathogen. Typically, the antigen is selected depending on the pathogen targeted by the vaccination.

For illustration only, the antigen can be a *Bordetella* antigen which is epicutaneously administered in combination with micro-perforation to provide vaccination against a *Bordetella* infection, such as pertussis.

Accordingly, the invention relates to an antigen from a pathogen for use for vaccinating a subject against said pathogen, wherein the antigen is administered to the subject by epicutaneous route, by means of a skin patch in combination with skin micro-perforation, preferably epidermal skin micro-perforation, performed at the site of application of said skin patch.

The invention further relates to a method for vaccinating a subject against a pathogen, which comprises:
micro-perforating an area of the skin of the subject, and
epicutaneously administering an antigen from the pathogen on said area of the skin, preferably by means of an occlusive skin patch.

The antigen is administered at an effective dose to the subject which means at a dose able to induce the desired immune response in the patient. Typically, the dose of antigen contained in the skin patch can vary depending on the subject in need of vaccination, in particular depending on his/her age, general condition and immune status (namely naïve or primed with respect to the pathogen), the immune effect which is sought, for instance priming or boosting vaccination, as well as the immunogenicity and the safety profile of the antigen. For instance, the dose of antigen that may be administered by application of the skin patch is from 5 µg to 200 µg. For instance, one can use a dose of recombinant or genetically detoxified PT ranging from 20 µg to 60 µg such as 25 µg or 50 µg.

As detailed above, the antigen may be present in dry form, optionally formulated with one or several pharmaceutical adjuvants, in the skin patch.

In some embodiments, the antigen is for providing priming vaccination against a pathogen in a subject. In other words, the invention is used to induce an immune response against the pathogen in a subject who is naïve with respect to the pathogen. Accordingly, the invention relates to the use of an antigen from a pathogen for providing priming vaccination against said pathogen in a subject, wherein the antigen is administered by epicutaneous route, by means of a skin patch, in combination with skin micro-perforation at the site of application of said skin patch in the subject.

In other embodiments, the Invention can be used for performing boosting vaccination. In that context, the invention may be useful to reactivate immunity against a pathogen or to improve, stimulate, enhance, expand and/or repolarize the pre-existing immune response against a pathogen. The pre-existing immune response may result from previous conventional vaccination of the subject against and/or natural exposure of the subject to the pathogen, e.g. in the context of pertussis vaccination, to a *Bordetella* pathogen, such as *Bordetella pertussis* or *Bordetella parapertussis*.

In some embodiments, the subject has been vaccinated with conventional priming vaccination during infanthood or childhood. Said conventional vaccination is typically performed by intramuscular or subcutaneous injection of one or several antigens from the pathogen of interest, in combination with adjuvant. For instance, in the context of pertussis vaccination, the subject may have been vaccinated with intramuscular or subcutaneous injection of one or several *Bordetella* antigens, such as toxoid of pertussis toxin, filamentous hemagglutinin and/or pertactin, in combination with adjuvant, during infanthood or childhood.

In some further embodiments, the invention resides in a method for providing immunization or vaccination against a pathogen, e.g. against *Bordetella* pathogen, to a subject in need thereof, said method comprising
a step of priming an immune response against the pathogen and
one or several steps of boosting said immune response.

In some embodiments, the priming step is performed by epicutaneously administering to the patient an antigen from the pathogen by means of a skin patch in combination with skin micro-perforation at the site of application of said patch.

In some further or alternate embodiments, one, several or all the subsequent boosting steps are performed by epicutaneously administering to the patient an antigen from the pathogen by means of a skin patch in combination with skin micro-perforation at the site of application of said patch.

In some other embodiments, the priming step is performed by conventional priming vaccination, typically by injecting an antigen through intramuscular or subcutaneous route to the patient, optionally in combination with adjuvant. In such embodiments, at least one subsequent boosting step comprises epicutaneously administering an antigen by means of a skin patch in combination with skin micro-perforation. In some embodiments, all the boosting steps comprise said combination.

For conventional priming, i.e. by injection (such as intramuscular or subcutaneous injection), the antigen is typically combined with an adjuvant. Suitable adjuvants include any substance that e.g., activates or accelerates the immune system to cause an enhanced antigen-specific immune response. Examples of adjuvants that can be used in the present invention include mineral salts, such as calcium phosphate, aluminum phosphate and aluminum hydroxide; immunostimulatory DNA or RNA, such as CpG oligonucleotides; proteins, such as antibodies or Toll-like receptor binding proteins; saponins e.g. QS21; cytokines; muramyl dipeptide derivatives; LPS; MPL and derivatives including 3D-MPL; GM-CSF (Granulocyte-macrophage colony-stimulating factor); imiquimod; colloidal particles; complete or incomplete Freund's adjuvant; Ribi's adjuvant or bacterial toxin e.g. cholera toxin or enterotoxin (LT). For conventional priming, a priming antigen composition is thus used, which comprises the antigen, typically in combination with an adjuvant. Such composition is generally in liquid form, suitable for injection. The composition may further comprise suitable excipients, such as a diluent, carrier, an isotonic solution, water, etc.

In the above embodiments, each antigen prime or boost may comprise several sequential applications of the skin patch, typically, between 1 and 5, preferably 1, 2 or 3. Each application may be separated from another by 1 day to several weeks, typically by 1 week to 8 weeks, preferably by 1, 2, or 3 weeks. The first antigen boost may be done any time after priming or exposure to the pathogen. Preferably, the first boosting is performed from 2 to 52 weeks, such as from 2 to 10 weeks, after priming.

For instance, the method of vaccination or immunization according to the invention comprises a prime immunization followed, typically 1-6 weeks later, preferably, 1, 2, 3 or 4 weeks later (e.g., 7, 14, 28 or 30 days later), by a single antigen boost immunization. If required, a second and, optionally, a third antigen boost can be performed. The second and third boosts may be performed within month time intervals, for example between 2-18 months after the previous boost.

The specific dose of antigen as well as the number of prime and/or boost applications and duration of contact can be adapted by the skilled artisan, depending on the subject, the nature of the antigen preparation etc. The treatment may be stopped at any time, e.g., once a sufficient immune response has been established.

It goes without saying that skin micro-perforation in the uses and methods according to the invention is performed as described above. In particular, the skin micro-perforation is preferably performed so as to obtain an array of microperforations which extend from the surface of the skin through the *stratum corneum* but without extending to the dermis and preferably without extending to the basal layer of the epidermis.

Particular Embodiments According to the Invention

A particular embodiment of the invention is the use of *Bordetella* antigen in the vaccination of a subject against *Bordetella*, wherein the antigen is administered by epicutaneous route by means of a skin patch in combination with skin micro-perforation at the site of application of said skin patch in the subject. The skin micro-perforation is limited to epidermis. The skin micro-perforation may be performed so as to form one or more microperforations on the skin, said microperforations extending from the surface of the skin through one or several epidermis layers, but without extending into the dermis. Preferably, the skin micro-perforation does not alter the basal layer of the epidermis. Typically, the microperforations may have a depth of less than 150 µm, preferably from 5 µm to 100 µm and/or a diameter of at most 200 µm, preferably from 5 µm to 150 µm. The microperforations may further form an array of micropores on the skin. The microporation density may be from 5% to 11%.

The skin micro-perforation may be performed prior to, or simultaneously with, the application of the skin patch. Preferably, the skin micro-perforation is performed immediately before the epicutaneous administration of the *Bordetella* antigen.

In some embodiments, the micro-perforation is performed by means of a laser micro-perforator, e.g. with the following settings:

Laser source: Er:YAG of 2940 nm,
Fluence of at most 16 $J/cm^2$,
Number of pulses: from 1 to 3,
Pulse duration from 15 µs to 100 µs, preferably from 50 µs to 100 µs.

The skin patch used to epicutaneously administer the *Bordetella* antigen may be occlusive and may comprise a backing suitable to create with the skin a hermetically closed chamber, and wherein the antigen is deposited on the skin facing side of said backing, in dry form, preferably without any adjuvant, and optionally in combination with one or several pharmaceutically acceptable excipients. The *Bordetella* antigen typically derives from *Bordetella pertussis* and is preferably selected from pertussis toxin (PT), filamentous hemagglutinin, pertactin, fimbria, adenylate cyclase toxin, tracheal cytotoxin, variants thereof, fragments thereof, detoxified forms thereof and combinations thereof.

For instance, the *Bordetella* antigen is a recombinant or genetically detoxified PT, e.g. comprising the mutations Arg9→Lys9 and Glu129→Gly129 in subunit S1 as compared to the sequence of wildtype PT.

The subject is preferably a human adult, e.g. a primed adult in need of a boosting vaccination against *Bordetella*. The subject may have been vaccinated against pertussis in his/her infanthood.

The following examples are given for purposes of illustration and not by way of limitation.

EXAMPLES

Example 1: Evaluation of the Impact of Laser Skin Micro-Perforation on Antigen Delivery Using Viaskin® Patches The aim of this experiment was to evaluate the impact of laser skin micro-perforation on antigen delivery using Viaskin® patches in BALB/c mice. Here, an infrared laser device (P.L.E.A.S.E. Professional developed by Pantec Biosolutions) was used. This device includes an Er:YAG laser source of 2940 nm wavelength that is able to generate an array of skin micropores by fractional ablation while preserving the surrounding tissues. Several laser settings were investigated so as to determine those enabling a micro-perforation through epidermis while preserving dermis, by histological observations. The expression of dermal pro-inflammatory cytokines was also assessed by qPCR for each testing settings. Laser setting corresponding to fluence of 2.8 J/cm$^2$ as described in Table 1 was selected for performing epidermis-limited skin micro-perforation.

TABLE 1

Description of the laser settings used in experiments conducted in mice

| Pulse Duration [µs] | Repetition rate [Hz] | Pulse per pore | Density [%] | Array size [mm] | Fluence [J/cm$^2$] | Approx. pore depth [µm] |
|---|---|---|---|---|---|---|
| 50 | 500 | 1 | 5 | 10 | 2.8 | 11 |

Indeed, this setting was shown to allow the specific targeting of epidermis while preserving dermis and inducing a mild dermal pro-inflammatory cytokines response mainly characterized by an upregulation of IL-b gene and, to a lesser extent, of IL-33 expression.

Laser Skin Micro Perforation Increases Trans-Epidermal Water Loss in Mice

As described in the background part of this application, the Viaskin® patch technology is based on the formation of an occlusive condensation chamber where antigen is solubilized by the skin-released humidity. To evaluate the effect of laser skin micro-perforation on skin water loss, BALB/c mice where treated with P.L.E.A.S.E device using the setting described in Table 1. Immediately after laser micro-perforation treatment, trans-epidermal water loss (TEWL) was measured. Skin laser micro-perforation strongly and significantly increases TEWL as compared to non-treated skin (mean TEWL value of 76±15 g/hm$^2$ for the 2.8 J/cm$^2$ laser treatment versus 7±3 g/hm$^2$ for non-treated skin [p<0.001]). These results suggest that laser skin micro-perforation could increase the level of humidity in the condensation chamber formed by Viaskin® patch, thus enhancing antigen solubilization from the surface of the patch backing.

Laser Skin Micro Perforation Increases Antigen Delivery by Viaskin® Patch in Mice To evaluate the impact of laser skin micro-perforation on antigen delivery to the skin, BALB/c mice where treated with P.L.E.A.S.E device using the setting described in Table 1. Immediately after laser micro-perforation treatment, mice received a Viaskin® patch loaded with ovalbumin conjugated to Alexa Fluor 647 fluorochrome (OVA-AF647). These patches were removed after 6 hrs and remaining OVA-AF647 was solubilized from the surface of the patch backing using ultrapure water. The quantity of remaining OVA-AF647 was estimated by measuring fluorescence intensity at 650 nm. A significant decrease of fluorescence intensity was observed for the patches originating from laser-treated mice compared to patches originating from non-treated mice (mean fluorescence value of 4,000±300 Relative Fluorescence Unit [RFU] for the 2.8 J/cm$^2$ laser treatment versus 4,700±300 RFU for non-treated skin [p<0.001]).

To visualize the impact of skin laser micro-perforation on antigen delivery and capture by skin DCs, skin biopsies have been collected from mice that received a Viaskin® patch loaded with ovalbumin conjugated to Alexa Fluor 488 fluorochrome (OVA-AF488) for 24 hrs on laser treated skin. Fluorescent microscopy results, obtained from skin cryosections showed a high AF488 signal in the epidermis, close to the basal membrane, for the mice that received skin laser micro-perforation. In the adjacent area of the dermis, an increase of the density of CMH-II positive cells was observed, some of which have captured OVA-AF488 antigen.

Overall, these results suggest that skin laser micro-perforation increases antigen delivery to the epidermis until basal membrane, thus increasing the quantity of antigen available for an uptake by skin dendritic cells. Moreover, micro-perforation also appears to promote a recruitment of MHC-II DC to the laser-treated area, thus increasing the pool of DC able to capture antigen.

Conclusion

The above results show that the combination of the skin patch antigen application with the mechanical skin optimization by laser skin micro-perforation (i) increases transepidermal water loss thus increasing the level of humidity in the condensation chamber of the patch and enhancing the antigen solubilization in the patch; and increases (ii) antigen delivery by skin patch.

Example 2: Evaluation of the Impact of Laser Skin Micro-Perforation on Antigen Uptake by Skin Dendritic Cells and their Migration to the Brachial Lymph Nodes The inventors aim to evaluate the impact of laser skin micro-perforation on the uptake of antigen administered using Viaskin® patch by skin dendritic cells (DC) and on their subsequent migration to the draining lymph nodes. For that, BALB/c mice where treated with P.L.E.A.S.E device using the setting described in Table 1.

Figure 1A:
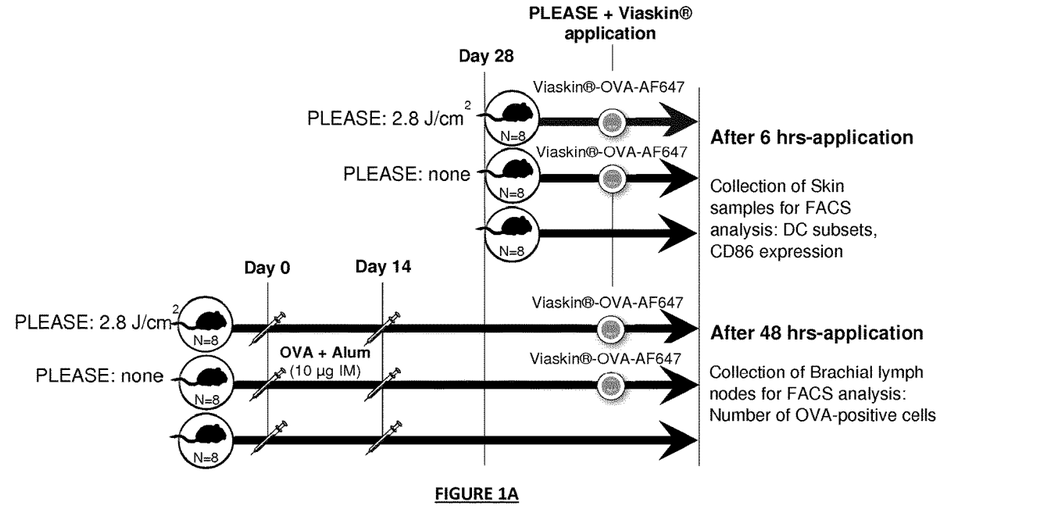
FIG. 1A shows the study design used for the evaluation of the impact of laser skin micro-perforation on antigen uptake by skin DC and their migration to the brachial lymph node. Female BALB/c mice, aged 6 weeks, have been depilated on the back using depilatory cream and treated with laser skin micro-perforation using the PLEASE device and the setting described in Table 1. Immediately after treatment, mice received Viaskin® patches loaded with 100 μg of OVA-AF647 for either 6 or 48 hrs. Skin samples have been collected 6 hrs after Viaskin® application whereas brachial draining lymph-nodes have been collected 48 hrs after Viaskin® application. As negative controls, mice received Viaskin®-OVA-AF647 without laser skin micro-perforation or were kept untreated. To evaluate the impact of laser skin micro-perforation on antigen uptake in primed mice, the same treatments were applied in mice previously immunized (primed) twice at two weeks' interval with 10 μg of OVA grade V mixed with aluminum hydroxide by intramuscular route.

Immediately after laser treatment, mice received Viaskin® patches loaded with 100 µg of OVA-AF647 for either 6 or 48 hrs (FIG. 1A). Skin samples were collected at 6 hrs post-application whereas brachial lymph-nodes were collected at 48 hrs post-application. As negative controls, mice received Viaskin®-OVA-AF647 without prior laser skin micro-perforation or were kept untreated (no laser micro-perforation, no Viaskin®-OVA-AF647).

Previous results have demonstrated that allergen uptake by skin DC and the migration of allergen-loaded DC to the lymph nodes was more efficient in mice that have been previously sensitized to the same allergen. In that context, the impact of laser skin micro-perforation on antigen uptake by skin DC and on their migration to the lymph node was also evaluated in primed mice. To that end, the same skin treatments as those described above (laser micro-perforation and Viaskin® application) were applied in mice previously immunized twice at two weeks' interval with 10 µg of OVA grade V by intramuscular route (FIG. 1A, three last groups).

Figures 1B, 1C:
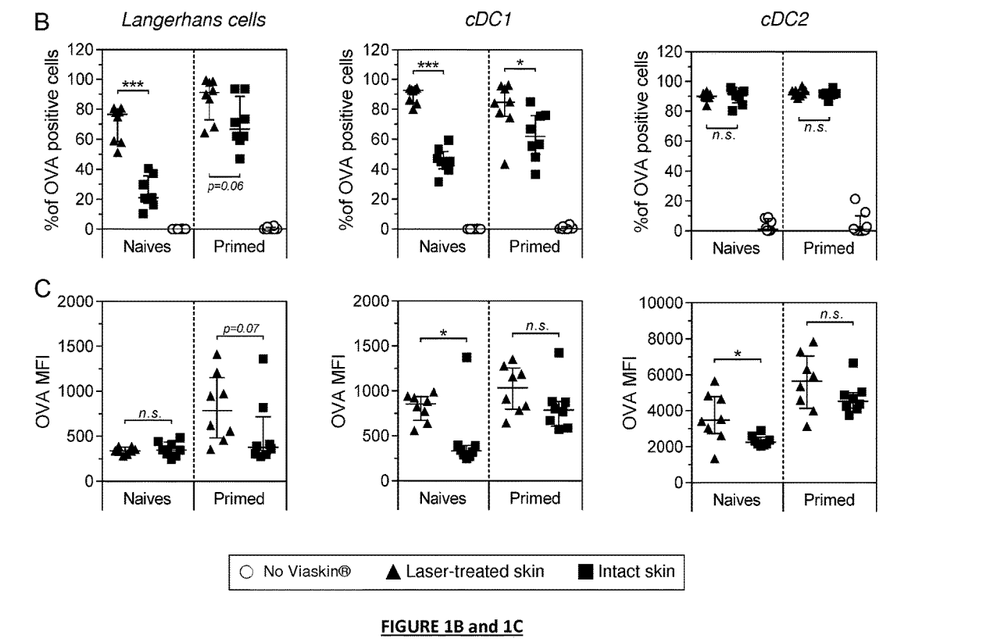

Laser Skin Micro Perforation Potentiates the Uptake of Antigen by Skin Dendritic Cells Upon Viaskin® Application As described in FIGS. 1B and 1C, skin samples have been collected 6 hrs after Viaskin®-OVA-AF647 application. Skin cells have been then isolated and labelled for FACS analysis. Three skin DC subsets have been differentiated i.e. Langerhans cells (LC), dermal XCR1 DC (cDC1) and dermal CD11b DC (cDC2). Then, the percentage of OVA-AF-647 positive cells was measured among LC and cDC1.

Viaskin® patch, when used on intact skin, enables a significant uptake of the antigen by skin dendritic cells as evidenced by the high mean of OVA-positive DC cells. Pre-treatment of the skin with epidermal skin micro-perforation potentiates the immune response with Viaskin® patch.

Indeed, a strong and significant increase of the percentage of OVA-AF647 positive cells was observed among the LC and the cDC1 that have been isolated from naïve mice that received laser skin micro-perforation before Viaskin® application, compared to mice for which Viaskin® was applied on intact skin (PLEASE: none) (mean percentages of 70±11% of OVA-positive LC upon laser treatment, compared to 24±10% of OVA-positive LC for intact skin [$p<0.001$]; mean percentages of 90±5% of OVA-positive cDC1 upon laser treatment, compared to 45±8% of OVA-positive cDC1 for intact skin [$p<0.001$]). The same trend was observed for mice that have been previously immunized to OVA (OVA-primed) (mean percentages of 87±13% of OVA-positive LC upon laser treatment, compared to 70±15% of OVA-positive LC for intact skin [$p=0.06$]; mean percentages of 81±16% of OVA-positive cDC1 upon laser treatment, compared to 63±15% of OVA-positive cDC1 for intact skin [$p<0.05$]) (see FIGS. 1B and 1C).

To evaluate the impact of laser skin micro-perforation on skin DC activation, the level of CD86 co-stimulation marker was evaluated for LC. A significant increase of CD86 expression was observed for the LC that have been isolated from both naïve and OVA-primed mice that received laser skin micro-perforation before Viaskin® application, compared to mice for which Viaskin® was applied on intact skin (Median of Fluorescence intensity (MFI) of 6500±700 in LC isolated from naïve mice laser treatment, compared to 4300±800 for intact skin [$p<0.01$]; MFI of 5000±1200 in LC isolated from OVA-primed mice upon laser treatment, compared to 3400±700 for intact skin [$p<0.05$]).

Conclusion

Overall, these results demonstrate that laser skin micro-perforation significantly increases the number of antigen-positive LC and cDC1 into the skin and the level of LC activation upon Viaskin® application.
Laser Skin Micro Perforation Increases the Number of Antigen Positive Skin-Originate Dendritic Cells in the Brachial Lymph Nodes Upon Viaskin® Application without Increasing the Free Passage of Antigen.

Figures 1D, 1E:
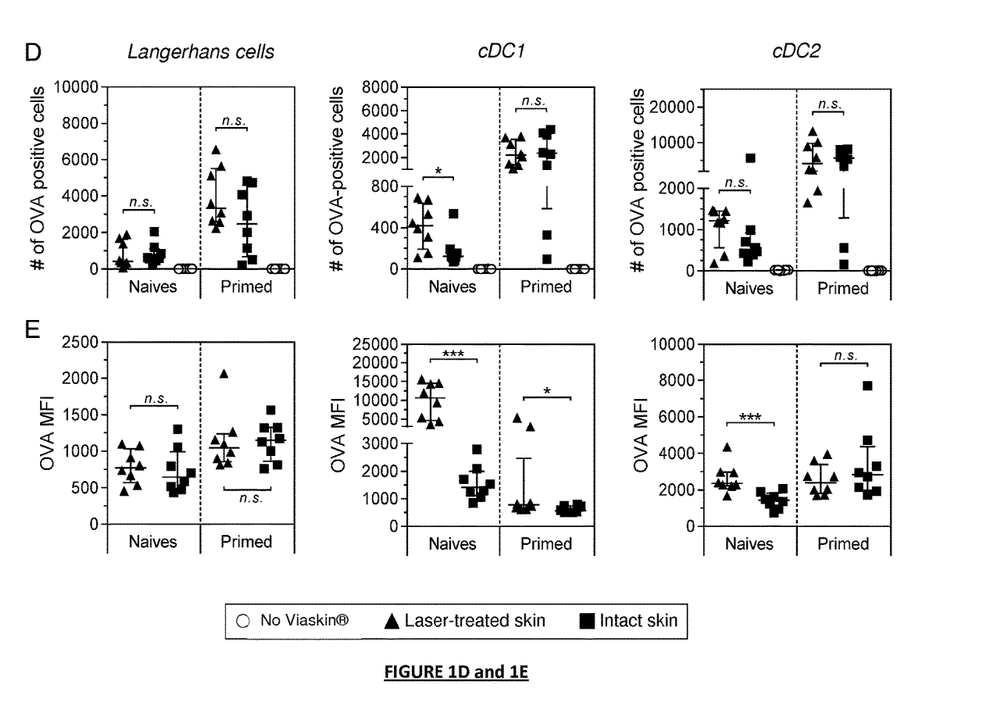
FIGS. 1D and 1E show the impact of epidermis-limited skin micro-perforation on the migration of OVA-positive cells to the draining lymph nodes. Brachial draining lymph nodes were collected, and cells were isolated and labelled as described above for FACS analysis. The absolute number of OVA-positive (AF-647-positive) cells (D) and the median of OVA-AF647 fluorescence intensity (MFI) (E) were measured among OVA-positive cells in each migratory DC subsets. Analyses were done for both naïve and OVA-primed mice, as indicated. (n=8 per experimental group). Median and interquartile ranges are shown. P values were determined according to the Mann-Whitney test (*, P<0.05; , P<0.01; *, P<0.001; n.s., non-significant).

As described in FIGS. 1D and 1E, brachial lymph nodes have been collected 48 hrs after Viaskin®-OVA-AF647 application. Lymph node cells have been then isolated from the four first groups (naïve mice) and labelled FACS analysis. Among the cells that have migrated from the skin, the three skin DC subsets (LC, cDC1 and cDC2) have been differentiated. Then, the absolute number of OVA-AF-647 positive cells was measured for each of these 3 subsets.

In naïve mice, laser skin micro-perforation treatment significantly increased the number of OVA-AF647 positive cDC1 in the draining lymph nodes compared to animals for which Viaskin® was applied on intact skin (mean number of OVA-positive cDC1 of 410±200 upon Viaskin® application on laser treated skin, compared to 170±140 upon Viaskin® application on intact skin [$p<0.05$]). Additionally, an increase in OVA-related MFI was observed for OVA-positive cDC1 and cDC2 isolated from mice that received Viaskin® patches on laser-treated skin compared to mice that received Viaskin® patches on intact skin (mean MFI of 9,900±4,600 for OVA-positive cDC1 isolated in naïve mice that received Viaskin® patches on laser-treated skin, compared to 1,600±580 for OVA-positive cDC1 isolated in naïve mice that received Viaskin® patches on intact skin [$p<0.001$]; mean MFI of 2,600±760 for OVA-positive cDC2 isolated in naïve mice that received Viaskin® patches on laser-treated skin, compared to 1,400±420 for OVA-positive cDC2 isolated in naïve mice that received Viaskin® patches on intact skin [$p<0.001$]) (see FIGS. 1D and 1E).

In order to validate the absence of free passage of antigen in laser treated mice, the number of OVA-positive B-cells was measured from brachial lymph nodes. The number of OVA-positive B-cells and the MFI corresponding to OVA fluorescence in OVA-positive B-cells were similar between the mice that received a Viaskin® patch on laser-treated skin and those that received Viaskin® patches on intact skin. This suggests that skin preparation using laser micro-perforation-targeting epidermal layers does not promote free systemic passage of antigen following Viaskin® patch application.

Conclusion

Overall, these results demonstrate that laser skin micro-perforation significantly increases the migration of antigen-positive cDC1 to the skin-draining lymph nodes and significantly increases the quantity of antigen that have been transported by cDC1 and cDC2. Additionally, laser skin micro-perforation does not promote free systemic passage of antigen following Viaskin® patch application whereby the combination epidermal micro-perforation/Viaskin® should have a similar safety profile as Viaskin® patch applied on intact skin.

Figure 2:
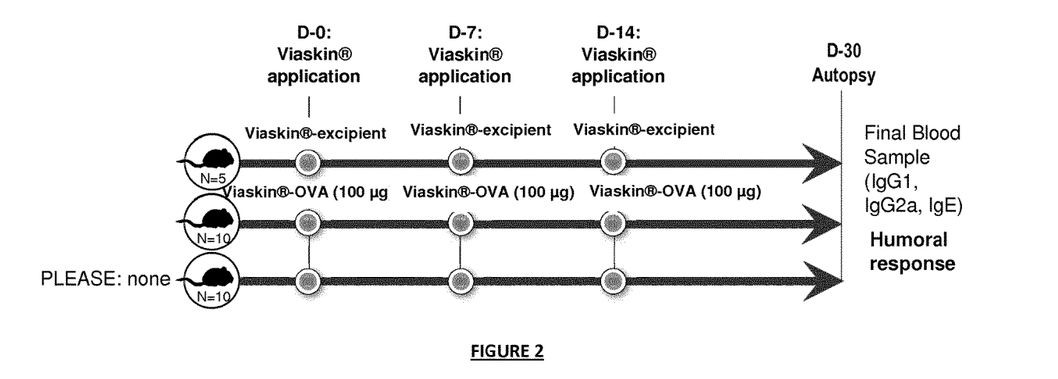
FIG. 2 shows the study design used for the evaluation of the impact of laser skin micro-perforation on the induction of specific humoral and cellular responses induced upon Viaskin®-OVA immunization. Female BALB/c mice (n=10 per experimental group), aged 6 weeks, have been depilated on the back using depilatory cream and treated with laser skin micro-perforation using the PLEASE device and the setting described in Table 1. Immediately after treatment, mice received Viaskin® patches loaded with 100 μg of OVA grade V (Viaskin®-OVA) for 48 hrs. This step was repeated 3 times during 3 constitutive weeks. As a negative control, mice received 3 Viaskin® loaded with PBS (Viaskin®-excipient) during 3 constitutive weeks. Blood samples have been collected two weeks after the last immunization for the evaluation of specific humoral response. Additionally, spleens have been collected two weeks after the last immunization for the evaluation of the specific cellular response.

Example 3: Evaluation of the Impact of Laser Skin Micro-Perforation on the Efficacy of Epicutaneous Vaccination with Viaskin® Loaded with an OVA Antigen The inventors investigated the impact of laser skin micro-perforation on the efficacy of prime or boost vaccination using Viaskin® patches. For that, BALB/c mice were divided into two sets of 2 groups (FIG. 2). The first set have been primed using Viaskin® patches loaded with 100 μg of OVA used as a model antigen and boosted twice at one-week interval using the same patches. Before each Viaskin® application, mice were treated by skin laser micro-perforation using the setting described in Table 1.
Laser Skin Micro Perforation Increases the Level of the Specific Humoral Response Induced by Viaskin® Immunization.

A strong and significant increase of OVA-specific IgG1 titers was observed for the mice that have been primed and boosted using Viaskin®-OVA after previous skin laser micro-perforation treatment compared to mice that have been primed and boosted using Viaskin®-OVA without laser treatment: mean IgG1 titers of 470±333 μg/ml with laser treatment, versus 82±47 μg/ml without laser treatment [$p<0.0001$].

Conclusion

Overall, these results indicate that skin laser micro-perforation strongly increases specific IgG1 antibody titers upon Viaskin® prime and/or boost immunizations with an OVA model antigen. In other words, epidermal micro-perforation potently enhanced the induction of specific immunity following epicutaneous immunization with Viaskin®.

Figure 3:
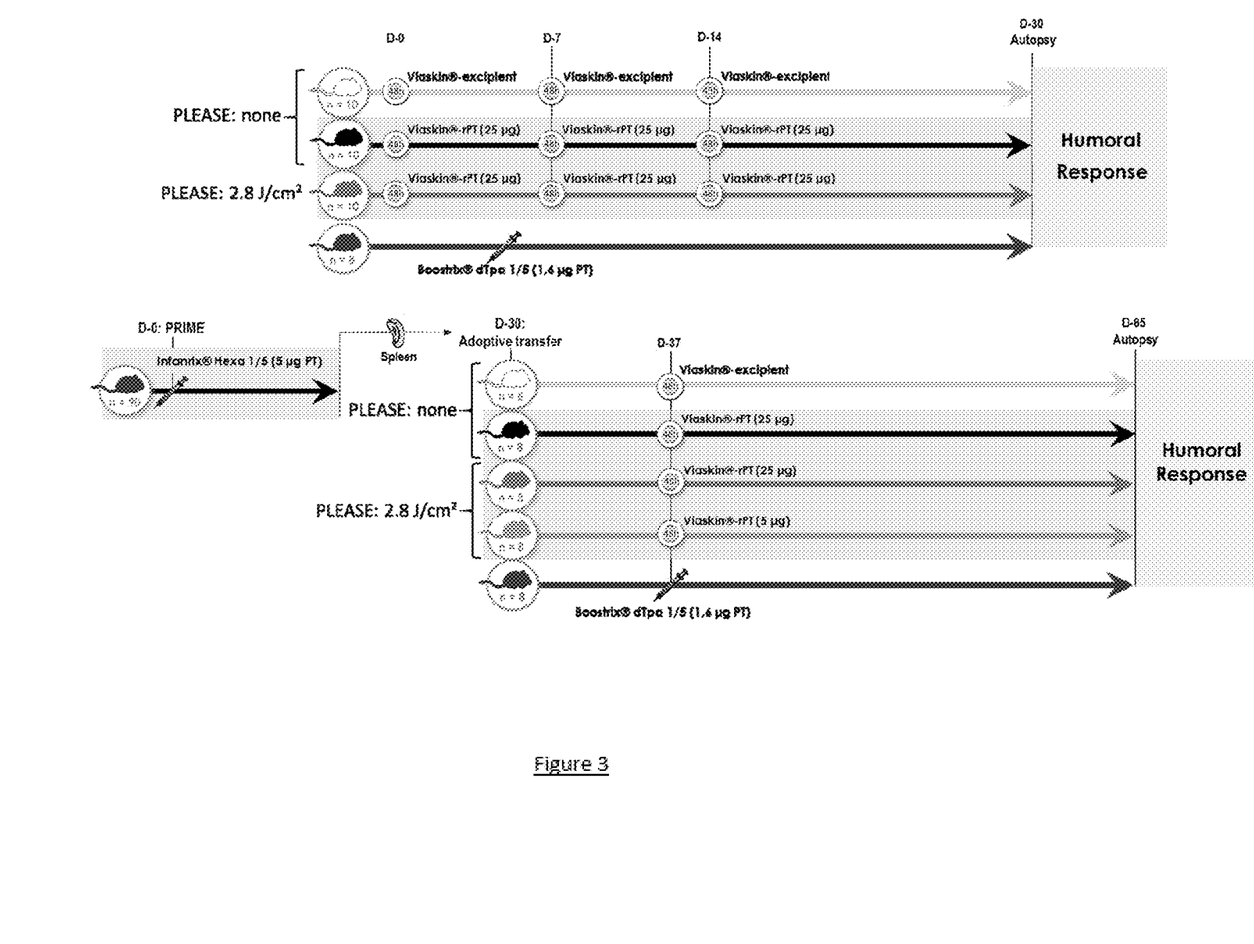

Example 4: Evaluation of the Impact of Laser Skin Micro-Perforation on the Efficacy of Epicutaneous Vaccination with Viaskin® Loaded with Recombinant Pertussis Toxin (rPT) in Mice The inventors investigated the impact of laser skin micro-perforation on the efficacy of prime or/and boost vaccination to rPT using Viaskin® patches. For that, BALB/c mice were divided into two sets of 4 and 5 groups (FIG. 3). The first set was primed using Viaskin® patches loaded with 25 µg of rPT and boosted twice at one-week interval using the same patches (prime/boost immunization). Before each Viaskin® application, mice were treated, or not, by skin laser micro-perforation using the settings described in the below Table 3. The fluence setting was shown to allow the specific targeting of epidermis without altering dermis.

As a negative control, mice received 3 Viaskin® loaded with excipient (PBS) and, as a positive control, mice received a single injection of Boostrix® (1.6 µg of chemically detoxified pertussis toxin equivalent, GSK) by intramuscular route. The second set of mice received an adoptive transfer of memory splenocytes isolated from Infanrix®-immunized mice (5 µg of chemically detoxified pertussis toxin equivalent by intramuscular route, GSK) following the procedure previously described (Gavillet at al., 2015). These recipient mice were boosted one week after adoptive transfer with one application of Viaskin® loaded with 5 or 25 µg of rPT after, or not, skin laser micro-perforation treatment (boost immunization). As a negative control, mice received one Viaskin® patch loaded with excipient (PBS), and as a positive control, mice were boosted with a single injection of Boostrix® (1.6 µg of chemically detoxified pertussis toxin equivalent, GSK) by intramuscular route. Blood samples were collected at day 30 for the first set of mice and at day 65 for the second set of mice, for the measurement of PT-specific antibody titers by ELISA.

TABLE 3

Description of the laser setting used in this experiment

| Pulse Duration [µs] | Repetition rate [Hz] | Pulse per pore | Density [%] | Array size [mm] | Fluence [J/cm$^2$] | Approx. pore depth [µm] |
|---|---|---|---|---|---|---|
| 50 | 500 | 1 | 8 | 10 | 2.8 | 11 |

Laser Skin Micro Perforation Increases the Level of the Specific Humoral Response Induced by Viaskin®-rPT Prime/Boost Immunization.

A significant increase of rPT-specific IgG titers was observed for the mice that have been primed and boosted using Viaskin®-rPT combined with previous skin laser micro-perforation treatment compared to mice that have been primed and boosted using Viaskin®-rPT without laser treatment (mean IgG titers of 5.9±0.3 Log 10 for laser treated mice, compared to 5.4±0.5 Log 10 for non-treated mice [p<0.01], versus 2.7±0.2 Log 10 for the negative control group [p<0.0001]). Additionally, antibody titers obtained from laser-treated mice were significantly higher to those obtained from Boostrix®-immunized mice (mean IgG titers of 5.3±0.2 for Boostrix®-immunized mice [p<0.001 compared to laser treated mice; non-significant compared to non-treated mice]).

Conclusion

These results indicate that skin laser micro-perforation enhances antibody responses induced by Viaskin®-rPT in mice, using a prime/boost immunization scheme. Moreover, antibody titers induced in mice treated with laser then primed and boosted with Viaskin®-rPT were higher than those induced by a single intramuscular injection of the commercial acellular pertussis booster vaccine containing chemically detoxified PT (Boostrix®).

Laser Skin Micro Perforation Increases the Level of the Specific Humoral Response Induced by Viaskin®-rPT Boost Immunization.

In mice that received memory splenocytes isolated from Infanrix®-primed animals, a significant increase of rPT-specific IgG titers was observed after boosting with Viaskin®-rPT (5 or 25 µg) combined with previous skin laser micro-perforation treatment compared to boosting with Viaskin®-rPT (25 µg) without laser treatment. Furthermore, antibody titers were similar between the two groups of mice treated with laser and boosted with Viaskin® loaded with either 5 or 25 µg of rPT (mean IgG titers of 6.4±0.2 Log 10 for mice treated with laser and boosted with Viaskin®-rPT (25 µg), compared to 6.4±0.1 Log 10 for mice treated with laser and boosted with Viaskin®-rPT (5 µg) [non-significant], versus 5.8±0.2 Log 10 for non-treated mice boosted with Viaskin®-rPT (25 µg) [p<0.0001]). Additionally, antibody titers obtained from mice treated with laser and boosted with Viaskin® rPT (5 or 25 µg) were significantly higher to those obtained from the mice boosted with Boostrix® (mean IgG titers of 6.1±0.1 Log 10 for Boostrix®-immunized mice [p<0.05 compared to mice treated with laser and boosted with Viaskin®-rPT (5 or 25 µg)].

Conclusion

These results indicate that skin laser micro-perforation enhances antibody responses induced by Viaskin®-rPT in mice used as boost vaccine. Importantly, antibody titers induced in mice treated with laser and boosted with Viaskin®-rPT were higher than those induced by the commercial acellular pertussis booster vaccine containing chemically detoxified PT (Boostrix®). Furthermore, these data show that skin laser micro-perforation allows a reduction of the dose of rPT loaded onto Viaskin® by 5 folds, without impairing the magnitude of antibody response.

Example 5: Evaluation of the Impact of Laser Skin Micro-Perforation on the Efficacy of Epicutaneous Vaccination with Viaskin® Loaded with Recombinant Pertussis Toxin (rPT) in Human The inventors investigated the impact of laser skin micro-perforation on the efficacy of boost vaccination to rPT using Viaskin® patches in human.

Initially, this phase I, first-in-human, randomized, double-blind, placebo-controlled, dose-escalation study was designed in order to evaluate the safety and the immunogenicity of a booster vaccination using Viaskin® patches combined with rPT at two dose levels (25 µg and 50 µg) in young healthy adults, on intact skin. In this first part of the study, 60 subjects received 2 applications of Viaskin®-rPT 25 µg (n=25), Viaskin®-rPT 50 µg (n=25) or Viaskin®-Placebo (n=10) at an interval of 14 days (±2 days). Viaskin® were applied during 48 h. Four weeks after the second Viaskin® patch application, all subjects received one intramuscular administration of Boostrix® dTpa for the recall of immunity against diphtheria, tetanus and the 3 pertussis antigens. Interim results showed that Viaskin®-rPT at the two doses was safe and well-tolerated. However, the immunogenicity of the booster vaccination with Viaskin®-rPT was low. Indeed, only 6.3% (95% CI [0.2%;30.2%]) and 13.3% (95% CI [1.7%;40.5%]) of subjects that received 25 µg or 50 µg doses, respectively, seroconverted after the second Viaskin®-rPT application.

In a second part of this study, 30 additional subjects have been randomized to receive 2 applications of either Viaskin®-rPT 25 µg (n=5) or Viaskin®-rPT 50 µg (n=25) in association with laser micro-perforation using the P.L.E.A.S.E. device (laser settings are detailed in Table 4). The 2 applications were performed at 2-weeks interval [at day 0 and day 14] and laser micro-perforation was performed before each patch application. Viaskin® were applied on micro-perforated skin during 48 h. Four weeks after the second Viaskin® patch application [day 42], all volunteers received one intramuscular administration of Boostrix® dTpa. By contrast to the first part of the study, 100% of the subjects that received Viaskin®-rPT 25 µg or Viaskin®-rPT 50 µg seroconverted after the second patch application among which 80% (95% CI [28.4%;99.5%]) and 88% (95% CI, [68.8%;97.5%]) respectively, presented at least 4-fold increase of anti-PT IgG titers at day 42. Conversely, 0% of the subjects that received placebo seroconverted after the second patch application. Furthermore, a high increase of anti-PT IgG titers was observed for individuals that received Viaskin®-rPT following skin laser micro-perforation compared to the placebo group (mean IgG titers of 46.40±34.80 IU/ml and 76.08±71.45 IU/ml for Viaskin®-rPT 25 µg- and Viaskin®-rPT 50 µg-treated groups, respectively, four weeks after the second patch application [day 42], compared to 5.25±4.29 for the placebo group [p=0.003 and p<0.001, respectively]). This corresponds to a fold increase (geometric mean ratio) of anti-PT IgG titers between day 0 and day 42 of 6.60 (mean 95% CI [2.47;17.63]) for the Viaskin®-rPT 25 µg-treated group, 10.35 (mean 95% CI [6.79;15.76]) for the Viaskin®-rPT 50 µg-treated group and 0.87 (mean 95% CI [0.72;1.05]) for the placebo group. Interestingly, these antibody responses were at the same range or even higher than antibody responses measured four weeks after Boostrix® dTpa injection (mean IgG titers of 59.75±53.12 [titers measured from the placebo group at day 70, four weeks after Boostrix® dTpa injection]).

TABLE 4

Description of the laser setting used in Pertussis clinical trial

| Pulse Duration [µs] | Power [W] | Pulse per pore | Density [%] | Array size [mm] | Fluence [J/cm²] | Approx. pore depth [µm] |
|---|---|---|---|---|---|---|
| 75 | 0.80 | 3 | 8 | 14 | 14.7 | 60 |

Conclusion

These results indicate that skin micro-perforation enhances antibody responses induced by Viaskin®-rPT booster vaccination in human. Importantly, antibody titers measured in volunteers that received Viaskin®-rPT associated with laser micro-perforation were at the same range than those induced by the commercial Boostrix® vaccine.

REFERENCES

Buasri W, Impoolsup A, Boonchird C, Luengchaichawange A, Prompiboon P, Petre, J, Panbangred W, 2012 Construction of *Bordetella pertussis* strains with enhanced production of genetically-inactivated Pertussis Toxin and Pertactin by unmarked allelic exchange. BMC Microbiology, 12: 61.

Gavillet B M, Mondoulet L, Dhelft V, Eberhardt C S, Auderset F, Pham H T et al., 2015 Needle-free and adjuvant-free epicutaneous boosting of pertussis immunity: Preclinical proof of concept. Vaccine, 33: 3450-5.

Mishra V., Mahor S., Rawat A., Dubey P., Gupta P N., Singh P., Vyas S P. et al, 2006. Development of novel fusogenic vesosomes for transcutaneous immunization. Vaccine 24, 5559-5570.

The invention claimed is:

1. A method for providing a boosting vaccination against a bacterial pathogen in a primed subject in need thereof, which comprises:
    performing skin micro-perforation in a skin area in the subject with a laser microporator so as to form an array of micropores, the skin micro-perforation not altering the basal layer of the epidermis and the array of micropores extending from the surface of the skin through one or several epidermis layers, but without extending to the dermis, and
    then epicutaneously administering an antigen from the bacterial pathogen on said skin area of the subject by means of a skin patch, wherein:
        the skin patch is occlusive and comprises a backing suitable to create a hermetically closed condensation chamber on skin, and wherein the antigen is deposited on the skin facing side of said backing, in dry form, and optionally in combination with one or several pharmaceutically acceptable excipients.

2. The method of claim 1, wherein the micropores do not extend beyond the *Stratus spinosum* in the epidermis.

3. The method of claim 2, wherein the micropores have a depth of less than 100 µm or a depth of 5 µm to 80 µm.

4. The method of claim 2, wherein the micropores have a diameter of at most 200 µm or a diameter of 5 µm to 150 µm.

5. The method of claim 1, wherein the array of micropores on the skin has a micropore depth from 10 µm to 70 µm, and a micropore density from 5% to 11%.

6. The method of claim 1, wherein the dose of bacterial antigen loaded in the patch is from 5 µg to 200 µg.

7. The method of claim 1, wherein the antigen is administered without adjuvant.

8. The method of claim 1, wherein the antigen is detoxified.

9. The method of claim 1, wherein the epicutaneous administration of the antigen by means of a skin patch in combination with skin micro-perforation is repeated.

10. The method of claim 1, wherein the antigen is selected from the group consisting of bacterial adherence factors and bacterial virulence factors.

11. The method of claim 1, wherein the method comprises administering a *Bordetella* antigen as the boosting vaccination.

12. The method of claim 11, wherein the *Bordetella* antigen is selected from the group consisting of pertussis toxin (PT), filamentous hemagglutinin, pertactin, fimbria, adenylate cyclase toxin, and tracheal cytotoxin.

13. The method of claim 11, wherein the subject is a primed human adult or teenager in need of a boosting vaccination against pertussis.

14. The method of claim 12, wherein the pertussis toxin (PT) from *Bordetella* is recombinant or a genetically detoxified.

15. The method of claim 1, wherein the method comprises administering a *Bordetella pertussis* antigen as the boosting vaccination.

16. A method for providing a boosting vaccination against *Bordetella pertussis* in a primed subject in need thereof, which comprises:
(i) performing skin micro-perforation in a skin area in the subject with a laser microporator, and
(ii) epicutaneously administering a detoxified pertussis toxin (PT) at an amount from 5 μg to 200 μg on said skin area of the subject by means of a skin patch which is applied on the micro-perforated skin area during at least 12 hours
wherein:
skin micro-perforation is performed so as to form an array of micropores on the skin with a micropore depth from 10 μm to 70 μm, and a micropore density from 5% to 11%, said micropores extending from the surface of the skin through one or several epidermis layers, but without extending to the dermis and the skin micro-perforation does not alter the basal layer of the epidermis;
the skin patch in step (ii) is occlusive and comprises a backing suitable to create a hermetically closed condensation chamber on skin, and wherein the antigen is deposited on the skin facing side of said backing, in dry form, and optionally in combination with one or several pharmaceutically acceptable excipients.

17. The method of claim 16, wherein the skin patch is applied on the micro-perforated skin area during about 48 hours and steps (i) and (ii) are repeated at two-weeks interval.

18. The method of claim 16, wherein the detoxified pertussis toxin is a genetically detoxified pertussis toxin.

19. The method of claim 18, wherein the dose of the detoxified pertussis toxin loaded in the patch ranges from 20 to 60 μg.

20. The method of claim 1, wherein the primed subject is a human adult.

21. The method of claim 16, wherein the primed subject is a human adult.

* * * * *